United States Patent
Yoshinaga et al.

(10) Patent No.: US 11,014,905 B2
(45) Date of Patent: May 25, 2021

(54) 2,6-DISUBSTITUTED PYRIDINE DERIVATIVE

(71) Applicant: Sumitomo Dainippon Pharma Co., Ltd., Osaka (JP)

(72) Inventors: Hidefumi Yoshinaga, Osaka (JP); Hiro Uemachi, Uji (JP); Tomomi Ohno, Toyonaka (JP); Jeremy Besnard, Dundee (GB)

(73) Assignee: SUMITOMO DAINIPPON PHARMA CO., LTD., Osaka (JP)

( * ) Notice: Subject to any disclaimer, the term of this patent is extended or adjusted under 35 U.S.C. 154(b) by 0 days.

(21) Appl. No.: 16/487,936

(22) PCT Filed: Mar. 12, 2018

(86) PCT No.: PCT/JP2018/009418
§ 371 (c)(1),
(2) Date: Aug. 22, 2019

(87) PCT Pub. No.: WO2018/168738
PCT Pub. Date: Sep. 20, 2018

(65) Prior Publication Data
US 2020/0039952 A1 Feb. 6, 2020

(30) Foreign Application Priority Data
Mar. 13, 2017 (JP) .............................. JP2017-046904

(51) Int. Cl.
| | | |
|---|---|---|
| C07D 401/04 | (2006.01) | |
| A61K 31/4545 | (2006.01) | |
| A61P 25/22 | (2006.01) | |
| C07D 405/14 | (2006.01) | |
| A61K 45/06 | (2006.01) | |

(52) U.S. Cl.
CPC ............ *C07D 401/04* (2013.01); *A61P 25/22* (2018.01); *C07D 405/14* (2013.01); *A61K 45/06* (2013.01)

(58) Field of Classification Search
CPC ................ C07D 401/04; C07D 405/14; A61K 31/4545; A61P 25/22; A61P 25/24
USPC .................................. 546/194, 193; 514/318
See application file for complete search history.

(56) References Cited

U.S. PATENT DOCUMENTS

| | | | |
|---|---|---|---|
| 4,977,167 A | 12/1990 | Matsumura et al. | |
| 5,321,035 A | 6/1994 | Matsumura et al. | |
| 9,732,065 B2 | 8/2017 | Yoshinaga et al. | |
| 10,800,755 B2 | 10/2020 | Yoshinaga et al. | |
| 2007/0093528 A1 | 4/2007 | Kuwabara et al. | |
| 2013/0064770 A1 | 3/2013 | Newington et al. | |

FOREIGN PATENT DOCUMENTS

| | | |
|---|---|---|
| EP | 0 580 398 | 1/1994 |
| JP | 59-29665 | 2/1984 |
| JP | 2009-249346 | 10/2009 |
| WO | 2011/150183 | 12/2011 |
| WO | 2014/192868 | 12/2014 |

OTHER PUBLICATIONS

Garcia-Garcia et al., "5-$HT_{1A}$ receptors in mood and anxiety: recent insights into autoreceptor versus heteroreceptor function", Psychopharmacology, vol. 231, No. 4, pp. 623-636 (2014).
Hachisu et al., The efficacy and the limitation at the clinical usage of anxiolytic agents, The Showa University Journal of Pharmaceutical Sciences, vol. 1, No. 1, pp. 17-28 (Jan. 5, 2010), with English Abstract.
Gobert et al., "Buspirone Modulates Basal and Fluoxetine-stimulated Dialysate Levels of Dopamine, Noradrenaline and Serotonin in the Frontal Cortex of Freely Moving Rats: Activation of Serotonin$_{1A}$ Receptors and Blockade of $_{α2}$-adrenergic Receptors Underlie its Actions", Neuroscience, vol. 93, No. 4, pp. 1251-1262, (1999).
Yoshino et al., "Tandospirone potentiates the fluoxetine-induced increases in extracellular dopamine via 5-$HT_{1A}$ receptors in the rat medial frontal cortex", Neurochemistry International, vol. 40, pp. 355-360 (2002).
Vandecapelle et al., "In vivo evaluation of 4-[$^{123}$I]iodo-N-{2-[4-(6-trifluoromethyl-2-pyridinyl)-1-piperazinyl]ethyl}benzamide, a potential SPECT radioligand for the 5-$HT_{1A}$ receptor", Nuclear Medicine and Biology, vol. 28, No. 6, pp. 639-643 (2001).
International Search Report (ISR) dated May 22, 2018 in International Patent Application No. PCT/JP2018/009418.

(Continued)

*Primary Examiner* — Charanjit Aulakh
(74) *Attorney, Agent, or Firm* — Wenderoth, Lind & Ponack, L.L.P.

(57) ABSTRACT

The present invention relates to a pyridine derivative of formula (1) wherein $R^1$ is optionally-substituted $C_{1-6}$ alkyl, optionally-substituted $C_{3-10}$ cycloalkyl, or optionally-substituted 5- to 10-membered saturated or partially-unsaturated heterocyclyl; $R^2$ is halogen atom, cyano, $C_{1-6}$ alkyl which may be optionally substituted with 1 to 3 the same or different halogen atoms, $C_{1-6}$ alkoxy which may be optionally substituted with 1 to 3 the same or different halogen atoms, or amino which may be optionally substituted with 1 to 2 the same or different $C_{1-6}$ alkyl; and the bind with broken line is single or double bond, or a pharmaceutically acceptable salt thereof, which is useful as a medicament for treating symptoms in anxiety-related disorder.

(1)

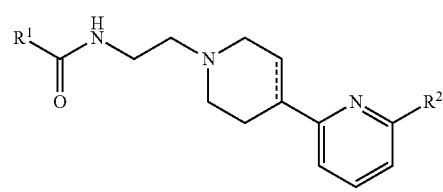

24 Claims, 7 Drawing Sheets

(56) References Cited

OTHER PUBLICATIONS

International Preliminary Report on Patentability (IPRP) dated Sep. 26, 2019 in International Patent Application No. PCT/JP2018/009418.
Extended European Search Report, dated Nov. 30, 2020 in corresponding European Patent Application No. EP 18 76 7940.
Office Action dated Oct. 27, 2020 in corresponding Singapore Patent Application No. 11201907935X.
Liegeois et al. "Enhancing a CH-π Interaction to Increase the Affinity for $5-HT_{1A}$ Receptors", ACS Med. Chem. Lett., Jan. 29, 2014, vol. 5, No. 4, pp. 358-362.
Abdala et al., "Pinpointing brainstem mechanisms responsible for autonomic dysfunction in Rett syndrome: therapeutic perspectives for $5-HT_{1A}$ agonists", Frontiers in Physiology, vol. 5, Article 2015, pp. 1-8 (2014).
Goetz et al., "Sarizotan as a Treatment for Dyskinesias in Parkinson's Disease: A Double-Blind Placebo-Controlled Trial", Movement Disorders, vol. 22, No. 2, pp. 179-186 (2007).
Ji et al., "Elevated DRD4 promoter methylation increases the risk of Alzheimer's disease in males", Molecular Medicine Reports, vol. 14, pp. 2732-2738 (2016).
Gadow et al., "Association of DRD4 polymorphism with severity of oppositional defiant disorder, separation anxiety disorder and repetitive behaviors in children with autism spectrum disorder", European Journal of Neuroscience, vol. 32, pp. 1058-1065 (2010).
Shaw et al., "Polymorphisms of the Dopamine $D_4$ Receptor, Clinical Outcome, and Cortical Structure in Attention-Deficit/Hyperactivity Disorder", Arch Gen Psychiatry, vol. 64, No. 8, pp. 921-931 (2007).

2,6-DISUBSTITUTED PYRIDINE DERIVATIVE

TECHNICAL FIELD

The present invention relates to a 2,6-disubstituted pyridine derivative or a pharmaceutically acceptable salt thereof which has dual agonism for serotonin 5-$HT_{1A}$ receptor and dopamine $D_4$ receptor; and a medicament for treating symptoms of anxiety-related disorder, comprising the derivative as an active ingredient.

BACKGROUND ART

Serotonin (5-hydroxytryptamine: 5-HT) is known as one of main neurotransmitters in central nervous system, and it is also known that serotonin is involved in various brain functions such as emotional reaction and cognitive function. Serotonin 5-$HT_{1A}$ receptor (hereinafter, referred to as "5-$HT_{1A}$ receptor") which is one of 5-HT receptor subtypes is highly expressed in cerebral cortex, hippocampus, raphe nucleus, amygdala, and the like. It is thought that anxiety or fear memory formation can be caused by the overactive of amygdala, and the activity of amygdala can be suppressed by stimulating 5-$HT_{1A}$ receptor. Thus, it is considered that a 5-$HT_{1A}$ agonist can suppressively control the neural circuit of anxiety/fear (Non-Patent Literature 1).

In addition, it is known that dopamine $D_4$ receptor (hereinafter, referred to as "$D_4$ receptor") which is one of dopamine receptor subtypes can also control the neural circuit of anxiety/fear formation. Specifically, $D_4$ receptor is present a lot in the medial prefrontal cortex which is a part of cerebral cortex, and the above-mentioned amygdala which is a responsible moiety for anxious formation also has a mutual neuron-connection to the medial prefrontal cortex. Thus, it is suggested that the stimulation to $D_4$ receptor can suppressively control the activity of amygdala to act on the control of anxiety/fear (Non-Patent Literature 2).

From the above-mentioned pharmacological viewpoint, it is expected that a drug having more potent and extensive antianxiety than existing 5-$HT_{1A}$ agonists can be created, if stimulating simultaneously both of 5-$HT_{1A}$ receptor and $D_4$ receptor to control the neural circuit function involved in anxiety from plural directions. However, any specific drugs having selective dual agonism for both the two receptors have not been reported.

Patent Literature 1 discloses pyridylpiperidine derivatives and the like which have $D_4$ receptor agonism. Patent Literature 2 discloses pyridylpiperazine derivatives and the like which are useful as an antianxiety drug.

PRIOR ART

Patent Reference

[Patent Literature 1] WO 2014/192868
[Patent Literature 2] JP S59-29665 A

Non-Patent Reference

[Non-Patent Literature 1] Psychopharmacology 2014, 231 (4), 623-36
[Non-Patent Literature 2] The Showa University Journal of pharmaceutical sciences, Vol. 1, No. 1, 2010, pp. 17-28.

SUMMARY OF INVENTION

Technical Problem

The purpose of the present invention may be to provide a new compound useful as a medicament for treating symptoms of anxiety-related disorder, which has dual agonism for 5-$HT_{1A}$ receptor and $D_4$ receptor.

Solution to Problem

The present inventors have extensively studied to reach the above purpose, and then have found that a compound of formula (1) shown below or a pharmaceutically acceptable salt thereof (hereinafter, it may be referred to as "the present compound") has dual agonism for 5-$HT_{1A}$ receptor and $D_4$ receptor. Based upon the new findings, the present invention has been completed.

The present invention can show as follows.

(Item 1)
A compound of formula (1):

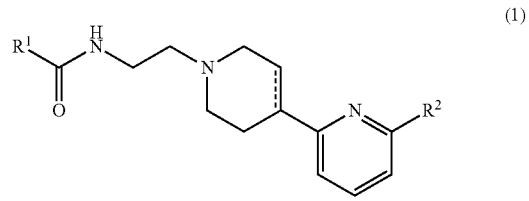

or a pharmaceutically acceptable salt thereof, wherein
$R^1$ is optionally-substituted $C_{1-6}$ alkyl, optionally-substituted $C_{3-10}$ cycloalkyl, or optionally-substituted 5- to 10-membered saturated or partially-unsaturated heterocyclyl group;
$R^2$ is halogen atom, cyano, $C_{1-6}$ alkyl which may be optionally substituted with 1 to 3 the same or different halogen atoms, $C_{1-6}$ alkoxy which may be optionally substituted with 1 to 3 the same or different halogen atoms, or amino which may be optionally substituted with 1 or 2 the same or different $C_{1-6}$ alkyl groups; and
the bond accompanied with broken line is single bond or double bond.

(Item 2)
The compound of Item 1 or a pharmaceutically acceptable salt thereof, wherein
$R^1$ is
(1) $C_{1-6}$ alkyl which may be optionally substituted with 1 to 3 the same or different substituents selected from the group consisting of halogen atom, hydroxy, $C_{3-7}$ cycloalkyl, and $C_{1-6}$ alkoxy,
(2) $C_{3-10}$ cycloalkyl which may be optionally substituted with 1 to 4 the same or different substituents selected from the group consisting of halogen atom, hydroxy, cyano, $C_{1-6}$ alkyl which may be optionally substituted with 1 to 3 the same or different halogen atom or $C_{1-6}$ alkoxy, $C_{1-6}$ alkoxy which may be optionally substituted with 1 to 3 the same or different halogen atom or $C_{1-6}$ alkoxy, and amino which may be optionally substituted with 1 or 2 the same or different $C_{1-6}$ alkyl, or
(3) 5- to 10-membered saturated or partially-unsaturated heterocyclyl group which may be optionally substituted with 1 to 4 the same or different substituents selected from the group consisting of halogen atom, hydroxy, cyano, $C_{1-6}$ alkyl which may be optionally substituted with 1 to 3 the same or different halogen atom or $C_{1-6}$ alkoxy, $C_{1-6}$ alkoxy which may be optionally substituted with 1 to 3 the same or different halogen atom or $C_{1-6}$ alkoxy, and amino which may be optionally substituted with 1 or 2 the same or different $C_{1-6}$ alkyl.

(Item 3)

The compound of Item 1 or 2, or a pharmaceutically acceptable salt thereof, wherein
R$^1$ is
(1) C$_{3-7}$ cycloalkyl which may be optionally substituted with 1 to 4 the same or different substituents selected from the group consisting of halogen atom, and C$_{1-6}$ alkyl which may be optionally substituted with 1 to 3 the same or different halogen atom or C$_{1-6}$ alkoxy, or
(2) 5- or 6-membered saturated or partially-unsaturated heterocyclyl group which may be optionally substituted with 1 to 4 the same or different substituents selected from the group consisting of halogen atom, and C$_{1-6}$ alkyl which may be optionally substituted with 1 to 3 the same or different halogen atom or C$_{1-6}$ alkoxy.

(Item 4)

The compound of any one of Items 1 to 3, or a pharmaceutically acceptable salt thereof, wherein R$^1$ is C$_{3-7}$ cycloalkyl which may be optionally substituted with 1 to 4 fluorine atoms, or 5- or 6-membered saturated or partially-unsaturated heterocyclyl group which may be optionally substituted with 1 to 4 fluorine atoms.

(Item 5)

The compound of any one of Items 1 to 4, or a pharmaceutically acceptable salt thereof, wherein R$^1$ is cyclohexyl which may be optionally substituted with 1 to 4 fluorine atoms, tetrahydropyranyl, tetrahydrofuryl, dihydropyranyl, or dihydrofuryl.

(Item 6)

The compound of any one of Items 1 to 5, or a pharmaceutically acceptable salt thereof, wherein R$^1$ is difluorocyclohexyl, or tetrahydropyranyl.

(Item 7)

The compound of any one of Items 1 to 6, or a pharmaceutically acceptable salt thereof, wherein R$^2$ is halogen atom, or C$_{1-6}$ alkyl which may be optionally substituted with 1 to 3 the same or different halogen atoms.

(Item 8)

The compound of any one of Items 1 to 7, or a pharmaceutically acceptable salt thereof, wherein R$^2$ is C$_{1-4}$ alkyl which may be optionally substituted with 1 to 3 fluorine atoms.

(Item 9)

The compound of any one of Items 1 to 8, or a pharmaceutically acceptable salt thereof, wherein the bond accompanied with broken line is single bond.

(Item 10)

The compound of Item 1 selected from the following compounds, or a pharmaceutically acceptable salt thereof,
4,4-difluoro-N-(2-{4-[6-(trifluoromethyl)pyridin-2-yl]piperidin-1-yl}ethyl)cyclohexane-carboxamide (Example 1),
N-{2-[4-(6-methylpyridin-2-yl)piperidin-1-yl]ethyl}-tetrahydro-2H-pyran-4-carboxamide (Example 8),
2,2-dimethyl-N-(2-{4-[6-(trifluoromethyl)pyridin-2-yl]piperidin-1-yl}ethyl)propanamide (Example 9), and
N-(2-{4-[6-(trifluoromethyl)pyridin-2-yl]piperidin-1-yl}ethyl)-tetrahydro-2H-pyran-4-carboxamide (Example 11).

(Item 11)

The compound of Item 1 selected from the following compounds, or a pharmaceutically acceptable salt thereof,
4,4-difluoro-N-(2-{4-[6-(trifluoromethyl)pyridin-2-yl]piperidin-1-yl}ethyl)cyclohexane-carboxamide (Example 1),
N-{2-[4-(6-methylpyridin-2-yl)piperidin-1-yl]ethyl}-tetrahydro-2H-pyran-4-carboxamide (Example 8), and
N-(2-{4-[6-(trifluoromethyl)pyridin-2-yl]piperidin-1-yl}ethyl)-tetrahydro-2H-pyran-4-carboxamide (Example 11).

(Item 12)

The compound of Item 1 of the following compound, or a pharmaceutically acceptable salt thereof,
4,4-difluoro-N-(2-{4-[6-(trifluoromethyl)pyridin-2-yl]piperidin-1-yl}ethyl)cyclohexane-carboxamide (Example 1).

(Item 13)

The compound of Item 1 of the following compound, or a pharmaceutically acceptable salt thereof,
N-{2-[4-(6-methylpyridin-2-yl)piperidin-1-yl]ethyl}-tetrahydro-2H-pyran-4-carboxamide (Example 8).

(Item 14)

The compound of Item 1 of the following compound, or a pharmaceutically acceptable salt thereof,
2,2-dimethyl-N-(2-{4-[6-(trifluoromethyl)pyridin-2-yl]piperidin-1-yl}ethyl)propanamide (Example 9).

(Item 15)

The compound of Item 1 of the following compound, or a pharmaceutically acceptable salt thereof,
N-(2-{4-[6-(trifluoromethyl)pyridin-2-yl]piperidin-1-yl}ethyl)-tetrahydro-2H-pyran-4-carboxamide (Example 11).

(Item 16)

A medicament comprising the compound of any one of Items 1 to 15 or a pharmaceutically acceptable salt thereof as an active ingredient.

(Item 17)

A medicament for treating generalized anxiety disorder, major depression, obsessive-compulsive disorder, Parkinson's disease, Rett syndrome, attention-deficit hyperactivity disorder, autism spectrum disorder, or dementia, comprising the compound of any one of Items 1 to 15 or a pharmaceutically acceptable salt thereof as an active ingredient.

(Item 18)

A method for treating generalized anxiety disorder, major depression, obsessive-compulsive disorder, Parkinson's disease, Rett syndrome, attention-deficit hyperactivity disorder, autism spectrum disorder, or dementia, comprising administering a therapeutically effective amount of the compound of any one of Items 1 to 15 or a pharmaceutically acceptable salt thereof to a patient in need thereof.

(Item 19)

Use of the compound of any one of Items 1 to 15 or a pharmaceutically acceptable salt thereof, in the preparation of a medicament for treating generalized anxiety disorder, major depression, obsessive-compulsive disorder, Parkinson's disease, Rett syndrome, attention-deficit hyperactivity disorder, autism spectrum disorder, or dementia.

(Item 20)

The compound of any one of Items 1 to 15 or a pharmaceutically acceptable salt thereof, for use in the treatment of generalized anxiety disorder, major depression, obsessive-compulsive disorder, Parkinson's disease, Rett syndrome, attention-deficit hyperactivity disorder, autism spectrum disorder, or dementia.

(Item 21)

A medicament comprising the compound of any one of Items 1 to 15 or a pharmaceutically acceptable salt thereof, and at least one other medicament selected from drugs classified as an antianxiety drug or an antidepressant drug.

(Item 22)

A medicament for treating generalized anxiety disorder, major depression, obsessive-compulsive disorder, Parkinson's disease, Rett syndrome, attention-deficit hyperactivity disorder, autism spectrum disorder, or dementia, comprising the compound of any one of Items 1 to 15 or a pharmaceutically acceptable salt thereof, which is used in combination with at least one other medicament selected from drugs classified as an antianxiety drug or an antidepressant drug.

(Item 23)

The medicament of Item 21 or 22, wherein the antianxiety drug is a selective serotonin reuptake inhibitor.

(Item 24)

The medicament of Item 23, wherein the selective serotonin reuptake inhibitor is at least one drug selected from the group consisting of sertraline, escitalopram, fluvoxamine, fuoxetine, paroxetine, clomipramine, and pharmaceutically acceptable salts thereof.

(Item 25)

The medicament of any one of Items 21 to 24, wherein the antidepressant drug is a serotonin reuptake inhibitor.

(Item 26)

The medicament of Item 25, wherein the serotonin reuptake inhibitor is at least one drug selected from the group consisting of milnacipran, duloxetine, venlafaxine, amoxapine, clomipramine, nortriptyline, imipramine, vortioxetine, and pharmaceutically acceptable salts thereof.

Effect of the Invention

The present compound has dual agonism for $5\text{-}HT_{1A}$ receptor and $D_4$ receptor. In a preferred embodiment, the present compound has a good metabolic stability, provides a long disappearance half-life ($T_{1/2}$), and exhibits a weak inhibitory action to a different GPCR, dopamine $D_2$ receptor (hereinafter, referred to as "$D_2$ receptor") and hERG channel. Thus, some preferred compounds of the present invention are useful as a medicament for treating symptoms in anxiety-related disorder, which has a long persistence effect in human body and a high safety.

DESCRIPTION OF EMBODIMENTS

Figure 1:
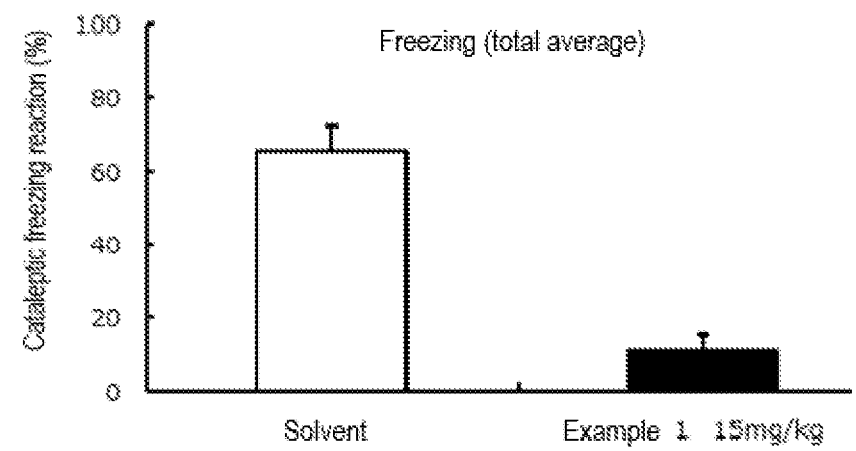
FIG. 1 shows the results of the compounds of Examples 1, 8, and 11 in the contextual fear conditioning test (Test 6).
Figure 1:
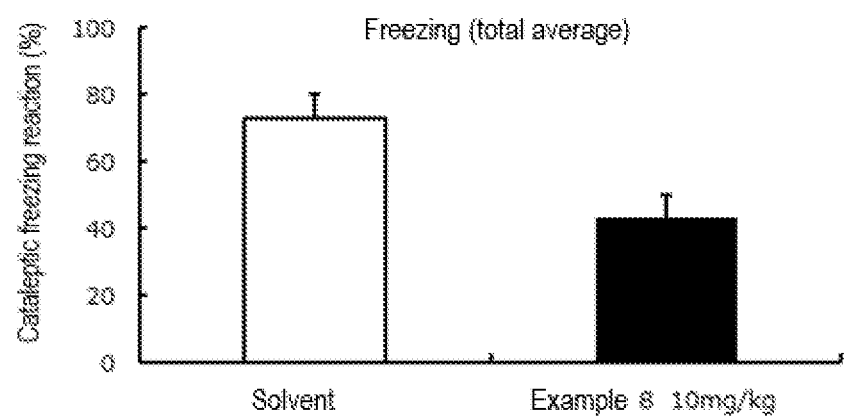
Figure 1:
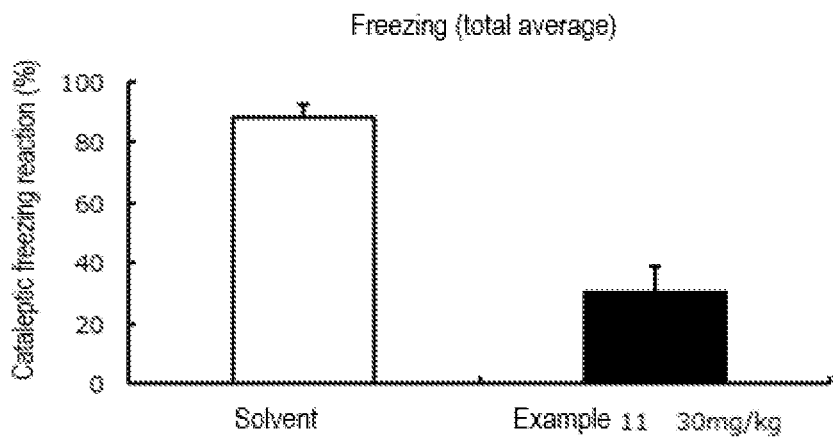

Hereinafter, the present invention is described in detail. In the description, the number of carbon atoms in the definition of "substituents" can indicates, for example, "$C_{1-6}$". The specific definition "$C_{1-6}$ alkyl" means an alkyl group having 1 to 6 carbon atoms.

The "halogen atom" includes, for example, fluorine atom, chlorine atom, bromine atom, and iodine atom.

The "$C_{1-6}$ alkyl" used herein means straight or branched chain saturated hydrocarbon group having 1 to 6 carbon atoms. Preferably, it is "$C_{1-4}$ alkyl group". The "$C_{1-6}$ alkyl group" includes, for example, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, and 2-ethylbutyl.

The "$C_{3-10}$ cycloalkyl" used herein means 3- to 10-membered saturated or partially-unsaturated mono-cyclic or multiple-cyclic hydrocarbon group. The "partially-unsaturated" means a state wherein the ring structure has one or some unsaturated bond(s), but it does not become a completely unsaturated aromatic ring (hereinafter, the same definition of "partially-unsaturated" applies). Preferably, it is "$C_{3-7}$ cycloalkyl". The "$C_{3-10}$ cycloalkyl" includes, for example, cyclopropyl, cyclobutyl, cyclopentyl, cyclohexyl, cyclopentenyl, and cyclohexenyl.

The "$C_{1-6}$ alkyl" moiety in the "$C_{1-6}$ alkoxy" is as defined in the aforementioned "$C_{1-6}$ alkyl". Preferably, it is "$C_{1-4}$ alkoxy". The "$C_{1-6}$ alkoxy" includes, for example, methoxy, ethoxy, propoxy, isopropoxy, butoxy, isobutoxy, sec-butoxy, and tert-butoxy.

The "5- to 10-membered saturated or partially-unsaturated heterocyclyl group" includes, for example, 5- to 10-membered saturated or partially-unsaturated mono-cyclic or multiple-cyclic heterocyclyl group which has 1 to 3 the same or different atoms selected from the group consisting nitrogen atom, oxygen atom, and sulfur atom. Specifically, it includes dihydropyranyl, tetrahydropyranyl, dihydrofuryl, tetrahydrofuryl, aziridinyl, azetidinyl, pyrrolidinyl, imidazolidinyl, piperidinyl, piperazinyl, azepanyl, morpholinyl, and thiomorpholinyl. The binding site of each group may be any atom of the carbon atoms and the nitrogen atoms which compose the ring.

Preferably, it includes 5- or 6-membered saturated heterocyclyl group. More preferably, it includes the following formulae (11), (12), (13), and (14).

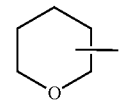

(11)

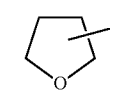

(12)

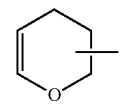

(13)

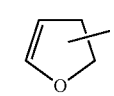

(14)

Wherein the binding bar crossing each ring means that the "binding bar" attaches at a substitutable site of the ring. More preferably, it is the group of formula (11).

The substituent in the "optionally-substituted $C_{1-6}$ alkyl" includes, for example, halogen atom, hydroxy, $C_{3-7}$ cycloalkyl, and $C_{1-6}$ alkoxy, preferably fluorine atom.

The substituent in the "optionally-substituted $C_{3-10}$ cycloalkyl", or the "optionally-substituted 5- to 10-membered saturated or partially-unsaturated heterocyclyl group" includes, for example, (a) halogen atom,
(b) hydroxy,
(c) cyano, (d) $C_{1-6}$ alkyl which may be optionally substituted with 1 to 3 the same or different halogen atom or $C_{1-6}$ alkoxy, (e) $C_{1-6}$ alkoxy which may be optionally substituted with 1 to 3 the same or different halogen atom or $C_{1-6}$ alkoxy, and (f) amino which may be optionally substituted with 1 or 2 the same or different $C_{1-6}$ alkyl.

Preferably, it is halogen atom, or $C_{1-6}$ alkyl which may be optionally substituted with 1 to 3 the same or different halogen atom or $C_{1-6}$ alkoxy; more preferably fluorine atom.

In the present compound of formula (1), the bond accompanied with broken line, $R^1$, and $R^2$ are preferably the following ones, but should not be limited thereto.

The bond accompanied with broken line is preferably single bond.

$R^1$ includes, preferably, (1) $C_{3-7}$ cycloalkyl which may be optionally substituted with 1 to 4 the same or different substituents selected from the group consisting of halogen atom, and $C_{1-6}$ alkyl which may be optionally substituted with 1 to 3 the same or different halogen atom or $C_{1-6}$ alkoxy, and (2) 5- or 6-membered saturated or partially-unsaturated heterocyclyl group which may be optionally substituted with 1 to 4 the same or different substituents selected from the group consisting of halogen atom, and $C_{1-6}$ alkyl which may be optionally substituted with 1 to 3 the same or different halogen atom or $C_{1-6}$ alkoxy.

$R^1$ includes, more preferably, $C_{3-7}$ cycloalkyl which may be optionally substituted with 1 to 4 fluorine atoms, and 5- or 6-membered saturated or partially-unsaturated heterocyclyl group which may be optionally substituted with 1 to 4 fluorine atoms. Even more preferably, $R^1$ includes cyclohexyl which may be optionally substituted with 1 to 4 fluorine atoms, tetrahydropyranyl, tetrahydrofuryl, dihydropyranyl, and dihydrofuryl. More preferably, $R^1$ includes difluorocyclohexyl, and tetrahydropyranyl. More preferably, $R^1$ includes 4,4-difluorocyclohexyl, and 4-tetrahydropyranyl.

$R^2$ includes, preferably, halogen atom, and $C_{1-6}$ alkyl which may be optionally substituted with 1 to 3 the same or different halogen atoms. More preferably, $R^2$ includes $C_{1-4}$ alkyl which may be optionally substituted with 1 to 3 fluorine atoms; even more preferably, $R^2$ includes methyl which may be optionally substituted with 1 to 3 fluorine atoms.

The compound of formula (1) can exist as a tautomer thereof. Thus, the compound of the present invention also includes a tautomer of compound (1).

The compound of formula (1) can have at least one chiral carbon atom. Thus, the compound of the present invention also includes a racemate of compound (1) as well as an optically active compound (1). When the compound of formula (1) has two or more chiral carbon atoms, the compound can be a stereoisomeric form. Thus, the compound of the present invention also includes a stereoisomer thereof and a mixture of stereoisomers.

In addition, the compound of formula (1) in which any one or more 1H atoms are replaced by $^2$H(D) atoms (deuterium form) is also within the scope of the present invention of formula (1).

The compound of formula (1) and a pharmaceutically acceptable salt thereof may be also in a form of hydrate and/or solvate, thus the compound of the present invention encompasses such hydrate thereof and solvate thereof such as ethanolate. In addition, the compound of the present invention also includes various embodiments of its crystal form.

The pharmaceutically acceptable salt of the compound of formula (1), when the compound has an acidic group, includes, for example, alkali metal salts such as sodium salt and potassium salt; alkaline earth metal salts such as calcium salt and magnesium salt; inorganic metal salts such as zinc salt; and organic base salts such as triethylamine, triethanolamine, tri(hydroxymethyl)aminomethane, and amino acid.

The pharmaceutically acceptable salt of the compound of formula (1), when the compound has a basic group, includes, for example, inorganic acid salts such as hydrochloride, hydrobromide, sulfate, phosphate, and nitrate; and organic acid salts such as acetate, propionate, succinate, lactate, malate, tartrate, citrate, maleate, fumarate, methanesulfonate, p-toluenesulfonate, benzenesulfonate, and ascorbate.

Hereinafter, the processes to prepare the present compound of formula (1) are explained along with examples, but the present invention should not be limited thereto.

Preparation Process

The compounds of the present invention can be prepared by means of the preparation processes mentioned below, or processes combined with known processes.

Each compound appearing in the following schemes may be also in its salt form, and such salts may include, for example, the corresponding salts exemplified as the salt of the compound of formula (1). The reactions mentioned below are just examples, thus the compounds of the present invention may be prepared by other means based on the knowledge of a skilled person in organic synthesis.

If there is a function group that needs to be protected in the preparation processes mentioned below, the function group may be protected as appropriate and then deprotected after completing the reaction or the reaction sequences, even though the use of any protecting groups is not specifically indicated.

The protecting group used herein includes, for example, general protecting groups described in T. W. Greene and P. G. M. Wuts, "*Protective Groups in Organic Synthesis*", 3rd Ed., John Wiley and Sons, inc., New York (1999); in more detail, it includes, for example, benzyloxycarbonyl, tert-butoxycarbonyl, acetyl, and benzyl, for amino group; and trialkylsilyl, acetyl, and benzyl, for hydroxy group. The protection and deprotection can be carried out by conventional means in organic synthesis chemistry (for example, the methods described in T. W. Greene and P. G. M. Wuts, "*Protective Groups in Organic Synthesis*", 3rd Ed., John Wiley and Sons, inc., New York (1999)), or similar means to them.

Preparation Process 1

The compound of formula (1) can be prepared, for example, by the following process.

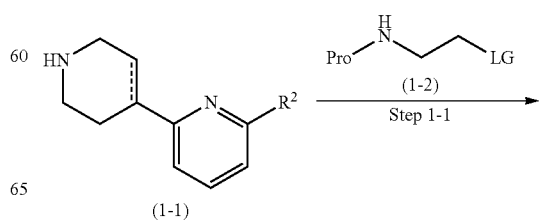

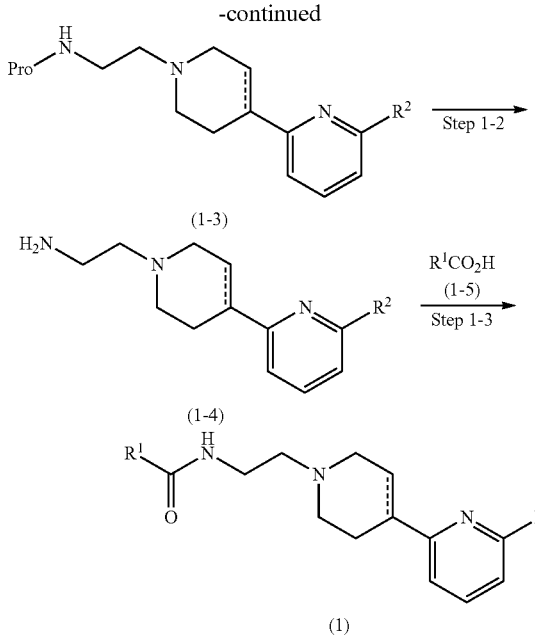

Wherein $R^1$ and $R^2$ are as defined in the above Item 1; the bond accompanied with broken line is single bond or double bond; LG is leaving group such as iodine atom, bromine atom, chlorine atom, and substituted sulfonyl (e.g. methanesulfonyl, p-toluenesulfonyl, etc.); Pro is a protective group for amino group.

Step 1-1: Preparation Step of Compound (1-3)

Compound (1-3) can be prepared by reacting Compound (1-1) and Compound (1-2) in a suitable solvent in the presence or absence of a base. The step may be carried out in the presence of a base if necessary, or in the presence of a phase-transfer catalyst if necessary. The reaction temperature is generally about −20° C. to boiling point of a solvent used herein. The reaction time depends on the reaction condition such as the reaction temperature, the condensing agent used herein, the starting material, and the reaction solvent, which is generally about 10 minutes to 48 hours.

Compound (1-1) can be got as a marketed product or can be prepared by a known synthetic method (for example, WO 2014/192868).

Compound (1-2) can be got as a marketed product or can be prepared by a known synthetic method (for example, J. Org. Chem. 1988, 53, 2226-2232).

The base used herein includes, for example, organic bases such as triethylamine, diisopropylethylamine, and pyridine; inorganic bases such as potassium carbonate, sodium carbonate, cesium carbonate, potassium bicarbonate, sodium bicarbonate, potassium dihydrogenphosphate, dipotassium hydrogenphosphate, potassium phosphate, sodium dihydrogenphosphate, disodium hydrogenphosphate, sodium phosphate, potassium hydroxide, sodium hydroxide, and sodium hydride; and metallic alkoxides such as sodium methoxide and potassium tert-butoxide.

The phase-transfer catalyst used herein includes, for example, tetrabutylammonium hydrogen sulfate.

The inert solvent used herein includes, for example, halogenated solvents such as chloroform and dichloromethane; aromatic hydrocarbons such as benzene and toluene; ether solvents such as diethyl ether, tetrahydrofuran (THF), and 1,4-dioxane; lower alcohol solvents such as methanol, ethanol, and 2-propanol; aprotic polar solvents such as acetonitrile, acetone, methylethylketone, dimethylformamide, N-methyl-2-pyrrolidinone, and dimethylsulfoxide; and mixture solvents thereof.

Step 1-2: Preparation Step of Compound (1-4)

Compound (1-4) can be prepared by removing the protective group for amino group (Pro) in Compound (1-3) in a known manner (for example, Protective Groups in Organic Synthesis, 3rd Ed. edited by Theodora W. Green, Peter G. M. Wuts, issued by John Wiley & Sons Inc., in 1999).

Step 1-3: Preparation Step of Compound (1)

Compound (1) can be prepared by reacting Compound (1-4) with the carboxylic compound of formula (1-5) in the presence of a condensing agent in an inert solvent. The reaction may be carried out further in the presence of a base. The reaction temperature is generally about −20° C. to boiling point of a solvent used herein. The reaction time depends on the reaction condition such as the reaction temperature, the condensing agent used herein, the starting material, and the reaction solvent, which is generally about 10 minutes to 48 hours.

Compound (1) can be also prepared by reacting Compound (1-4) with an acid halide or acid anhydride derived from Compound (1-5) in the presence of a base in an inert solvent. The reaction temperature is generally about −20° C. to boiling point of a solvent used herein. The reaction time depends on the reaction condition such as the reaction temperature, the condensing agent used herein, the starting material, and the reaction solvent, which is generally about 10 minutes to 48 hours.

The condensing agent used herein includes, for example, dicyclohexylcarbodiimide (DCC), diisopropylcarbodiimide (DIPC), 1-ethyl-3-(3-dimethylaminopropyl)-carbodiimide (WSC), benzotriazol-1-yl-tris(dimethylamino)phosphonium hexafluorophosphate (BOP), diphenylphosphonylazide (DPPA), N,N-carbonyldiimidazole (CDI), and benzotriazol-1-yl-N,N,N',N'-tetramethyluronium hexafluorophosphate (HBTU). If necessary, an additive such as N-hydroxysuccinimide (HOSu), 1-hydroxybenzotriazole (HOBt), and 3-hydroxy-4-oxo-3,4-dihydro-1,2,3-benzotriazine (HOOBt) may be added to the reaction.

The base used herein includes, for example, organic bases such as triethylamine, diisopropylethylamine, and pyridine; inorganic bases such as potassium carbonate, sodium carbonate, cesium carbonate, potassium bicarbonate, sodium bicarbonate, potassium dihydrogenphosphate, dipotassium hydrogenphosphate, potassium phosphate, sodium dihydrogenphosphate, disodium hydrogenphosphate, sodium phosphate, potassium hydroxide, sodium hydroxide, and sodium hydride; and metallic alkoxides such as sodium methoxide and potassium tert-butoxide.

The inert solvent used herein includes, for example, halogenated solvents such as chloroform and dichloromethane; aromatic hydrocarbons such as benzene and toluene; ether solvents such as diethyl ether, tetrahydrofuran (THF), and 1,4-dioxane; aprotic polar solvents such as acetonitrile, acetone, methylethylketone, dimethylformamide, N-methyl-2-pyrrolidinone, and dimethylsulfoxide; basic solvents such as pyridine; and mixture solvents thereof.

Preparation Process 2

The compound of formula (1-1b) can be prepared from the compound of formula (1-1a) by the following process.

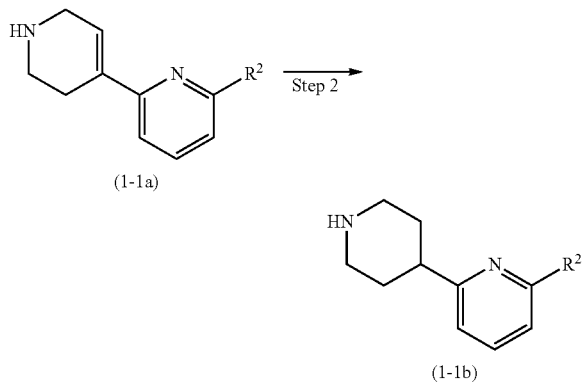

(1-1a)

(1-1b)

Wherein R² is as defined in the above Item 1.

Step 2: Preparation Step of Compound (1-1b)

Compound (1-1b) can be prepared by hydrogenating Compound (1-1a) under pressureless or pressured hydrogen atmosphere in a suitable inert solvent. The catalyst used in the present reduction reaction includes, for example, palladium catalyst such as palladium carbon, rhodium catalyst such as rhodium carbon, platinum catalyst such as platinum carbon, and ruthenium catalyst such as ruthenium carbon. The reaction temperature is generally between 0° C. and 50° C. The reaction time depends on the reaction condition such as the reaction temperature, the catalyst used herein, the starting material, and the reaction solvent, which is generally about 10 minutes to 48 hours.

The inert solvent used herein includes, for example, ester solvents such as ethyl acetate; aromatic hydrocarbons such as benzene and toluene; ether solvents such as diethyl ether, tetrahydrofuran, 1,4-dioxane, and 1,2-dimethoxyethane; alcohol solvents such as methanol, ethanol, and 2-propanol; aprotic polar solvents such as dimethylformamide, N-methyl-2-pyrrolidinone, and dimethylsulfoxide; and mixture solvents thereof.

The other compounds of formula (1-1) can be got as a marketed product or can be prepared by a known synthetic method or a similar method thereof.

Preparation Process 3

The compound of formula (1-3b) can be also prepared from the compound (1-3a) by the following process.

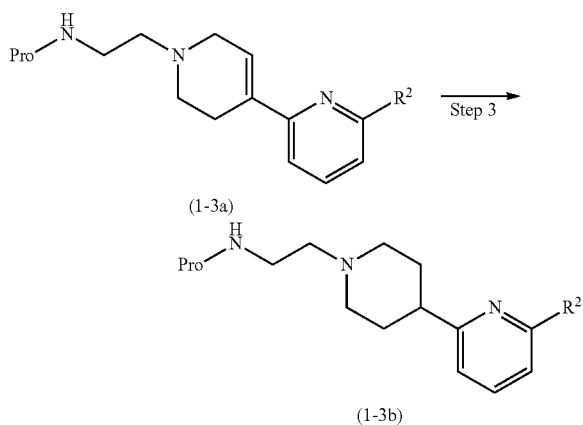

(1-3a)

(1-3b)

Wherein R² is as defined in the above Item 1; Pro is a protective group for amino group.

Step 3: Preparation Step of Compound (1-3b)

Compound (1-3b) can be prepared by hydrogenating Compound (1-3a) under pressureless or pressured hydrogen atmosphere in a suitable inert solvent. The catalyst used in the present reduction reaction includes, for example, palladium catalyst such as palladium carbon, rhodium catalyst such as rhodium carbon, platinum catalyst such as platinum carbon, and ruthenium catalyst such as ruthenium carbon. The reaction temperature is generally between 0° C. and 50° C. The reaction time depends on the reaction condition such as the reaction temperature, the catalyst used herein, the starting material, and the reaction solvent, which is generally about 10 minutes to 48 hours.

The inert solvent used herein includes, for example, ester solvents such as ethyl acetate; aromatic hydrocarbons such as benzene and toluene; ether solvents such as diethyl ether, tetrahydrofuran, 1,4-dioxane, and 1,2-dimethoxyethane; alcohol solvents such as methanol, ethanol, and 2-propanol; aprotic polar solvents such as dimethylformamide, N-methyl-2-pyrrolidinone, and dimethylsulfoxide; and mixture solvents thereof.

The present compound having a desired functional group at a desired position can be prepared by suitably combining the above preparation processes. The isolation and purification of each intermediate or product in the above preparation processes can be carried out by conventional manners in organic synthesis, for example, by suitably combining filtration, extraction, washing, drying, concentration, crystallization, various chromatography, etc.

Or, some intermediates may be sometimes used in the next step without purification.

Some starting compounds or intermediates in the above preparation processes can exist in a salt form such as hydrochloride, but can be used as free form thereof. When starting compounds or intermediates that are in salt form need to be used or obtained as free form thereof, they can be transformed to free forms thereof by dissolving or suspending them in an appropriate solvent and neutralizing the solution or suspension with a base such as aqueous sodium bicarbonate.

Some of the compound of formula (1) or a pharmaceutically acceptable salt thereof can exist as isomers such as tautomer (for example, keto-enol form), regioisomer, geometrical isomer, and optical isomer. The present invention encompasses every possible isomer including the above, and a mixture thereof which has various mixture proportions. And, optical isomers thereof can be resolved by a known manner such as chromatography with an optically-active column and fractional crystallization at a suitable step in the above-mentioned preparation processes. And, an optically-active starting material can be also used for this purpose.

In order to obtain the compound of formula (1) as a salt thereof, when the product is a salt of the compound of formula (1), the product should be directly purified; or when the product is in free form of the compound of formula (1), the product should be dissolved or suspended in an appropriate solvent and then an acid or a base should be added thereto to form a salt thereof. And, some of compound (1) or a pharmaceutically acceptable salt thereof can exist as a hydrate thereof or a solvate thereof with various solvents, which are also included in the present invention.

5-HT$_{1A}$ receptor is highly expressed in cerebral cortex, hippocampus, raphe nucleus, amygdala, and the like. It is considered that anxiety or fear memory formation can be caused by the overactive of amygdala. The activity of amygdala can be suppressed by stimulating 5-$HT_{1A}$ receptor, thus it is considered that a 5-$HT_{1A}$ agonist can suppressively control the neural circuit of anxiety/fear (Non-Patent Literature 1). For example, buspirone and tandospirone which are 5-$HT_{1A}$ agonist are used as medicaments for treating generalized anxiety disorder (GAD). In addition, 5-$HT_{1A}$ agonist is expected to also become a medicament for treating CNS diseases besides GAD such as major depression, obsessive-compulsive disorder, Parkinson's disease, Rett syndrome, and dementia.

The preferably-used treatment of GAD includes, particularly, the improvement of psychiatric symptom and/or somatic symptom in GAD.

The preferably-used treatment of major depression includes, particularly, the improvement of psychiatric symptom and/or somatic symptom in major depression.

The preferably-used treatment of obsessive-compulsive disorder includes, particularly, the improvement of compulsion and/or obsession in obsessive-compulsive disorder.

The preferably-used treatment of Parkinson's disease includes, particularly, the improvement of the symptom of L-DOPA-induced dyskinesia in Parkinson's disease.

The preferably-used treatment of Rett syndrome includes, particularly, the improvement of symptom of apnea in Rett syndrome.

Dementia includes, for example, Alzheimer-type dementia and Lewy body dementia, and the preferably-used treatment of dementia includes, particularly, the treatment of peripheral symptom of the dementia (e.g. behavior disorder associated with Alzheimer-type dementia).

It is known that $D_4$ receptor controls the neural circuit involved in anxiety or fear formation. The stimulation of $D_4$ receptor highly-expressed in medial prefrontal cortex is expected to be able to suppressively control the activity of amygdala. Thus, $D_4$ agonist is expected to exhibit antianxiety, like 5-$HT_{1A}$ agonist.

Considering the above pharmacological knowledge, if both of 5-$HT_{1A}$ receptor and $D_4$ receptor can be simultaneously stimulated to control the neural circuit system involved in anxiety from plural directions, such medicament stimulating the both receptors is expected to exhibit more potent and broader antianxiety than existing 5-$HT_{1A}$ agonists.

In addition, the present compound has an agonism for $D_4$ receptor, thereby the present compound is expected to become a medicament for treating attention-deficit hyperactivity disorder (ADHD: which is ADHD defined in Diagnostic and Statistical Manual of Mental Disorders, 5th edition (DSM-5), and was a disease name classified as attention-deficit hyperactivity disorder in previous DSM-IV), and a CNS disease which shows a similar symptom to ADHD, for example, autism spectrum disorder (autism spectrum disorder defined in Diagnostic and Statistical Manual of Mental Disorders, 5th edition (DSM-5), and was a disease name classified as autism, Asperger syndrome, atypical pervasive developmental disorder, and childhood disintegrative disorder in previous DSM-IV), schizophrenia which shows a similar symptom to ADHD, mood disorder, cognitive impairment, etc.

In the treatment of ADHD, in particular, it includes, preferably, ADHD whose cardinal symptom is inattention, hyperactivity, and impulsivity.

In the treatment of autism spectrum disorder, in particular, it includes, preferably, autism spectrum disorder whose cardinal symptom is a continuous defect of social communication and social interaction, and a pattern of limited repetitive behavior, interest, action, etc.

The present compound has an agonism for 5-$HT_{1A}$ receptor and $D_4$ receptor. For example, the present compound exhibits $E_{max}$ value of 50% or more, which indicates a maximum agonist activity for 5-$HT_{1A}$ receptor and $D_4$ receptor, or $EC_{50}$ value of 100 nmol/L or less, which indicates an agonist activity (Test 1).

In addition, the present compound has a potent binding affinity to 5-$HT_{1A}$ receptor and $D_4$ receptor (Test 2). In a preferred embodiment, the binding affinity of the present compound to 5-$HT_{1A}$ receptor and $D_4$ receptor is 100 or more times potent compared with that of $D_2$ receptor, thus the present compound can exert the pharmacological effect based on 5-$HT_{1A}$ and $D_4$ receptor agonism, without reaching the blood level causing side effects such as extrapyramidal symptom and hyperprolactinemia which are thought to be caused by $D_2$ antagonistic action.

In another preferred embodiment, the present compound is expected to have a very small effect for cardiovascular system because there is a big difference between the inhibitory concentration of hERG channel which is an express indicator of arrhythmia in long QT, and the express concentration of the expected pharmacological effect (Test 5).

The disappearance half-life ($T_{1/2}$) of a medicament is a factor for determining the frequency of administration to retain the effect. It is thought that plural administrations of a medicament having a short $T_{1/2}$ per day can cause forgetting to take a medication or unfinishing taking a medication, which can hinder a suitable medication. Furthermore, if the frequency of administration increases, it is concerned that the incidence rate of side effects can increase or the tolerability can decrease in association with high-dose administration. From the viewpoint mentioned above, if a medicament having a long $T_{1/2}$ is found out, the medicament is expected to be a long-acting medicament with little concern mentioned above, which can bring in liability relief of medicated patients.

In a preferred embodiment of the present compound, the estimated human disappearance half-life ($T_{1/2}$) of the present compound is 8 hours or more (Test 4), it is expected that the drug efficacy can be retained for a long period in human body, the medication adherence of medicated patients can be improved, and a high tolerability can be exhibited at the administration.

The present compound can be orally or parenterally administered. In case of oral administration, the compound can be administered in conventionally-used dosage form. In case of parenteral administration, the compound can be administered in topical administration form, injection form, transdermal form, nasal form, etc. The oral form or the rectal administration form include, for example, capsule, tablet, pill, powder, cachet, suppository, and liquid. The injection includes, for example, aseptic solution and suspension. The topical administration form includes, for example, cream, ointment, lotion, and transdermal formulation (e.g. normal patch and matrix).

The above-mentioned dosage forms can be prepared with a pharmaceutically acceptable excipient and additive in a conventional manner. The pharmaceutically acceptable excipient and additive include carrier, binder, flavor, buffer, thickener, colorant, stabilizing agent, emulsifier, dispersant, suspending agent, and preservative.

The pharmaceutically acceptable carrier includes, for example, magnesium carbonate, magnesium stearate, talc, sugar, lactose, pectin, dextrin, starch, gelatin, tragacanth, methylcellulose, sodium carboxymethylcellulose, low-melting-point wax, and cocoa butter. The capsule form can be prepared by filling a capsule with the present compound and a pharmaceutically acceptable carrier. The present compound can be put into a capsule with or without a pharmaceutically acceptable excipient. The cachet can be also prepared in a similar manner.

The injectable liquid form includes solution, suspension, and emulsion, for example, water solution, water-propylene glycol, etc. The liquid form may comprise water, and also it may be prepared in a solution of polyethylene glycol or/and propylene glycol. The liquid form suitable for oral administration may be prepared by adding the present compound to water and also adding colorant, flavor, stabilizing agent, sweetener, solubilizer, thickener, etc. thereto, as appropriate. Alternatively, the liquid form suitable for oral administration may be prepared by adding the present compound with a dispersant to water and rendering the liquid sticky. The thickener used herein includes, for example, pharmaceutically acceptable natural or synthetic gum, resin, methylcellulose, sodium carboxymethylcellulose, and a known suspending agent.

The dose of each compound can depend on patient's disease, age, body weight, gender, symptom, and the administration route, etc. In general, the present compound is administered to an adult (body weight: 50 kg) by 0.1-1000 mg/day, preferably 0.1-300 mg/day, once a day or in 2-3 doses. Or, it may be administered once in a few days to a few weeks.

In order to enhance the effect and/or reduce the side effects thereof, the present compound and a pharmaceutically acceptable salt thereof may be used in combination with another drug. For example, the present compound may be used in combination with an antianxiety drug such as selective serotonin reuptake inhibitor. Or, for example, the present compound may be used in combination with an antidepressant drug such as serotonin reuptake inhibitor.

The selective serotonin reuptake inhibitor includes, for example, sertraline, escitalopram, fluvoxamine, fluoxetine, paroxetine, and clomipramine. The serotonin reuptake inhibitor includes, for example, milnacipran, duloxetine, venlafaxine, amoxapine, clomipramine, nortriptyline, imipramine, and vortioxetine. Hereinafter, drugs with which the present compound may be used in combination are abbreviated as "concomitant drug".

The administration interval of the present compound and its concomitant drug is not limited, i.e., the concomitant drug may be administered at the same time as the present compound or at a suitable interval. Or, the present compound and its concomitant drug can be formulated into a combination drug. The dose of the combination drug can be suitably determined based on the standard of the clinically-used dose thereof. The combination ratio of the present compound and its concomitant drug can be suitably determined based on its subject patient, administration route, disease, pathology, concomitant drug, etc. For example, when the subject patient is a human being, the concomitant drug may be used in 0.01 to 100 part by weight per part of the present compound. For the purpose of reducing the side effect, an antiemetic drug, a sleep-inducing drug, an anti-seizure drug, etc. may be used in combination as a concomitant drug.

EXAMPLES

The present invention is explained in more detail in the following by referring to Reference examples, Examples, and Tests; however, the technical scope of the present invention is not limited thereto. The compound names used in Reference examples and Examples are not always based on IUPAC nomenclature system. In order to simplify description, abbreviations are sometimes used, the meanings of which are as defined above. In the present description, the abbreviations shown below are sometimes used.

In the NMR data of Reference examples and Examples, the following abbreviations are used.

Me: methyl

DMF: N,N-dimethylformamide

THF: tetrahydrofuran tert-: tertiary $CDCl_3$: deuterated chloroform $DMSO-d_6$: deuterated dimethylsulfoxide Proton nuclear magnetic resonance spectra were measured with FT-NMR spectrometer (300 MHz or 400 MHz, JEOL). The chemical shifts were shown in δ value (ppm). The signs used in NMR denote the following meanings, δ is singlet, d is doublet, dd is double doublet, dt is double triplet, t is triplet, q is quartet, m is multiplet, br is broad, brs is broad singlet, and J is coupling constant.

Example 1

4,4-Difluoro-N-(2-{4-[6-(trifluoromethyl)pyridin-2-yl]piperidin-1-yl}ethyl)cyclohexane-carboxamide

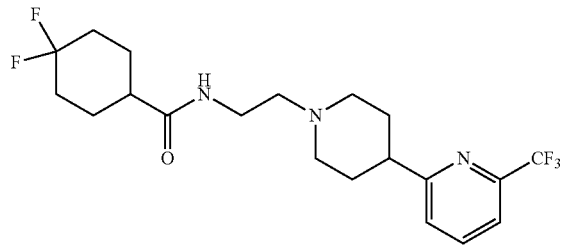 [SMILES: O=C(NCCN1CCC(c2cccc(C(F)(F)F)n2)CC1)C1CCC(F)(F)CC1]

To a mixture of the compound of Reference example 4 (600 mg), triethylamine (1.31 mL), 4,4-difluorocyclohexan-ecarboxylic acid (257 mg), and DMF (5.0 mL) was added O-(benzotriazol-1-yl)-N,N,N',N'-tetramethyluronium hexafluorophosphate (654 mg). The reaction mixture was stirred at room temperature for 8 hours, and water was added thereto. The mixture was extracted with ethyl acetate. The organic layer was dried over sodium sulfate, filtrated, and concentrated in vacuo. The residue was purified by silica gel column chromatography (chloroform/methanol) to give the title compound (406 mg).

$^1$H-NMR (400 MHz, $CDCl_3$) δ: 1.48-2.06 (10H, m), 2.09-2.30 (5H, m), 2.54 (2H, t, J=6.0 Hz), 2.77-2.88 (1H, m), 2.97-3.08 (2H, m), 3.38 (2H, dt, J=5.5, 5.5 Hz), 6.22 (1H, brs), 7.37 (1H, d, J=7.8 Hz), 7.52 (1H, d, J=7.8 Hz), 7.80 (1H, dd, J=7.8, 7.8 Hz).

Examples 2-7

According to the method of Example 1, Examples 2-7 were prepared from the corresponding Reference examples.

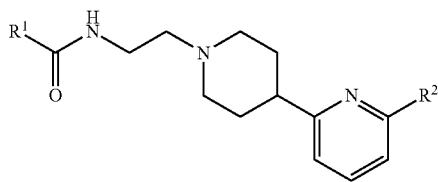

| Example | R¹— | R²— | Instrumental analyses data |
|---|---|---|---|
| 2 | (tetrahydropyran-4-yl) | —CF₃ | $^1$H-NMR (400 MHz, CDCl$_3$) δ: 1.55-1.67 (1H, m), 1.68-1.78 (1H, m), 1.79-2.02 (6H, m), 2.10-2.20 (2H, m), 2.40-2.48 (1H, m), 2.52 (2H, t, J = 6.1 Hz), 2.77-2.86 (1H, m), 2.98-3.04 (2H, m), 3.29-3.46 (2H, m), 3.57-3.64 (1H, m), 3.70 (1H, dd, J = 11.6, 7.9 Hz), 3.79 (1H, dt, J = 11.4, 4.6 Hz), 3.90 (1H, dd, J = 11.7, 3.7 Hz), 6.53 (1H, brs), 7.37 (1H, d, J = 7.8 Hz), 7.51 (1H, d, J = 7.6 Hz), 7.79 (1H, dd, J = 7.8, 7.8 Hz). |
| 3 | (oxabicyclic) | —Me | $^1$H-NMR (300 MHz, CDCl$_3$) δ: 1.55-1.67 (1H, m), 1.69-2.00 (9H, m), 2.07-2.21 (2H, m), 2.46-2.58 (5H, m), 2.62-2.75 (1H, m), 2.83-2.95 (1H, m), 2.95-3.05 (2H, m), 3.30-3.42 (2H, m), 4.59-4.71 (2H, m), 6.13 (1H, brs), 6.98 (2H, d, J = 7.9 Hz), 7.52 (1H, dd, J = 7.7, 7.7 Hz). |
| 4 | (4,4-difluorocyclohexyl) | —Me | $^1$H-NMR (300 MHz, CDCl$_3$) δ: 1.67-2.02 (10H, m), 2.07-2.28 (5H, m), 2.51 (2H, t, J = 5.9 Hz), 2.54 (3H, s), 2.63-2.75 (1H, m), 2.94-3.05 (2H, m), 3.33-3.40 (2H, m), 6.19 (1H, brs), 6.97 (1H, d, J = 7.7 Hz), 6.99 (1H, d, J = 7.5 Hz), 7.52 (1H, dd, J = 7.7, 7.7 Hz). |
| 5 | (Me₂C(CH₂OMe)CH₂-) | —Me | $^1$H-NMR (400 MHz, CDCl$_3$) δ: 1.17 (6H, s), 1.72-1.85 (2H, m), 1.92-2.00 (2H, m), 2.10-2.21 (2H, m), 2.49-2.54 (5H, m), 2.64-2.74 (1H, m), 2.98-3.05 (2H, m), 3.31-3.39 (4H, m), 3.42 (3H, s), 6.96 (1H, d, J = 7.8 Hz), 6.98 (1H, d, J = 7.6 Hz), 7.15 (1H, brs), 7.51 (1H, dd, J = 7.7, 7.7 Hz). |
| 6 | (Me₂C(CH₂OMe)CH₂-) | —CF₃ | $^1$H-NMR (400 MHz, CDCl$_3$) δ: 1.17 (6H, s), 1.82-1.99 (4H, m), 2.10-2.20 (2H, m), 2.51 (2H, t, J = 6.2 Hz), 2.75-2.85 (1H, m), 2.97-3.05 (2H, m), 3.32-3.40 (4H, m), 3.44 (3H, s), 7.35 (1H, d, J = 8.0 Hz), 7.50 (1H, d, J = 7.8 Hz), 7.78 (1H, dd, J = 7.8, 7.8 Hz). |
| 7 | (1-(methoxymethyl)cyclopropyl) | —CF₃ | $^1$H-NMR (400 MHz, CDCl$_3$) δ: 0.65 (2H, dd, J = 6.7, 4.0 Hz), 1.27 (2H, dd, J = 6.7, 4.0 Hz), 1.89-1.96 (4H, m), 2.12-2.20 (2H, m), 2.54 (2H, t, J = 6.2 Hz), 2.75-2.85 (1H, m), 3.00-3.07 (2H, m), 3.36-3.42 (2H, m), 3.46 (2H, s), 3.49 (3H, s), 7.34 (1H, d, J = 7.8 Hz), 7.50 (1H, d, J = 7.8 Hz), 7.61 (1H, brs), 7.77 (1H, dd, J = 7.8, 7.8 Hz). |

Example 8

N-{2-[4-(6-Methylpyridin-2-yl)piperidin-1-yl]ethyl}-tetrahydro-2H-pyran-4-carboxamide

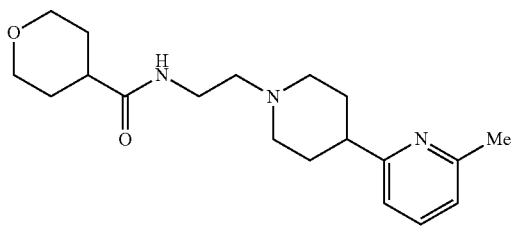 [SMILES: Cc1cccc(C2CCN(CCNC(=O)C3CCOCC3)CC2)n1]

To a mixture of the compound of Reference example 6 (500 mg), triethylamine (1.27 mL), and dichloromethane (5.0 mL) was added tetrahydro-2H-pyran-4-carbonylchloride (0.207 mL) under ice temperature. The reaction mixture was stirred at room temperature for 12 hours, and water was added thereto. The mixture was extracted with chloroform. The organic layer was dried over sodium sulfate, filtrated, and concentrated in vacuo. The residue was purified by silica gel column chromatography (chloroform/methanol) to give the title compound (451 mg).

$^1$H-NMR (300 MHz, CDCl$_3$) δ: 1.71-1.90 (6H, m), 1.91-2.01 (2H, m), 2.08-2.19 (2H, m), 2.31-2.43 (1H, m), 2.51 (2H, t, J=6.4 Hz), 2.54 (3H, s), 2.63-2.76 (1H, m), 2.95-3.04 (2H, m), 3.33-3.50 (4H, m), 3.99-4.07 (2H, m), 6.20 (1H, brs), 6.98 (1H, d, J=7.7 Hz), 6.99 (1H, d, J=7.7 Hz), 7.52 (1H, dd, J=7.7, 7.7 Hz).

Examples 9-10

According to the method of Example 8, Examples 9-10 were prepared from the corresponding Reference examples.

Example 11

N-(2-{4-[6-(Trifluoromethyl)pyridin-2-yl]piperidin-1-yl}ethyl)-tetrahydro-2H-pyran-4-carboxamide

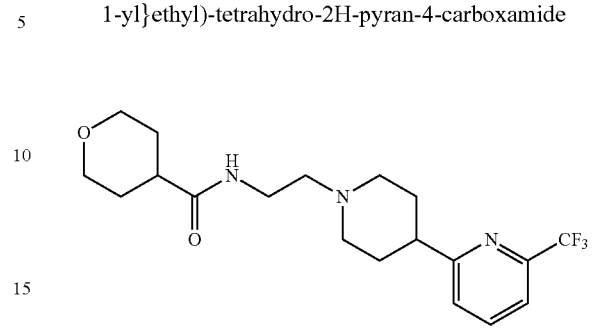

To a mixture of the compound of Reference example 4 (350 mg), triethylamine (0.765 mL), and dichloromethane (3.0 mL) was added tetrahydro-2H-pyran-4-carbonylchloride (0.124 mL) under ice temperature. The reaction mixture was stirred at room temperature for 12 hours, and water was added thereto. The mixture was extracted with chloroform. The organic layer was dried over sodium sulfate, filtrated, and concentrated in vacuo. The residue was purified by silica gel column chromatography (chloroform/methanol) to give the title compound (232 mg).

$^1$H-NMR (300 MHz, CDCl$_3$) δ: 1.71-2.02 (8H, m), 2.08-2.21 (2H, m), 2.32-2.44 (1H, m), 2.52 (2H, t, J=6.0 Hz), 2.75-2.88 (1H, m), 2.95-3.05 (2H, m), 3.33-3.50 (4H, m), 3.99-4.08 (2H, m), 6.15 (1H, brs), 7.37 (1H, d, J=8.1 Hz), 7.52 (1H, d, J=7.7 Hz), 7.79 (1H, dd, J=7.9, 7.9 Hz).

| Example | R$^1$— | R$^2$— | Instrumental analyses data |
|---|---|---|---|
| 9 | Me$_3$C— (tert-butyl) | —CF$_3$ | $^1$H-NMR (400 MHz, CDCl$_3$) δ: 1.21 (9H, s), 1.76-1.89 (2H, m), 1.95-2.04 (2H, m), 2.12-2.21 (2H, m), 2.53 (2H, t, J = 6.1 Hz), 2.77-2.87 (1H, m), 2.98-3.05 (2H, m), 3.32-3.37 (2H, m), 6.35 (1H, brs), 7.37 (1H, d, J = 7.8 Hz), 7.51 (1H, d, J = 7.6 Hz), 7.79 (1H, dd, J = 7.9, 7.9 Hz). |
| 10 | Me$_3$C— (tert-butyl) | —Me | $^1$H-NMR (300 MHz, CDCl$_3$) δ: 1.21 (9H, s), 1.68-1.83 (2H, m), 1.90-2.03 (2H, m), 2.10-2.21 (2H, m), 2.48-2.56 (5H, m), 2.63-2.76 (1H, m), 2.95-3.04 (2H, m), 3.30-3.37 (2H, m), 6.38 (1H, brs), 6.98 (2H, d, J = 7.7 Hz), 7.52 (1H, dd, J = 7.7, 7.7 Hz). |

Example 12

4,4-Difluoro-N-{2-[6-(trifluoromethyl)-3',6'-dihydro[2,4'-bipyridin]-1'(2'H)-yl]ethyl}-cyclohexane-1-carboxamide

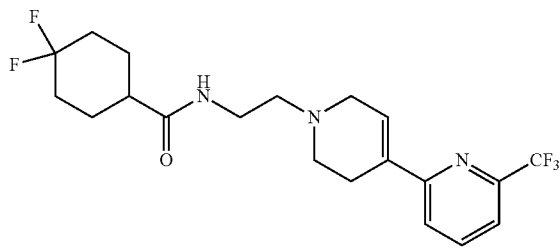 [SMILES: O=C(NCCN1CC=C(c2cccc(C(F)(F)F)n2)CC1)C1CCC(F)(F)CC1]

A mixture of 4,4-difluorocyclohexane-1-carboxylic acid (42.0 mg), triethylamine (0.178 mL), 1-[bis(dimethylamino)methylene]-1H-benzotriazolium-3-oxide hexafluorophosphate (89.0 mg), and N,N-dimethylformamide (1.0 mL) was stirred at room temperature for 20 minutes, and the compound of Reference example 7 (81.2 mg) was added thereto. The reaction mixture was stirred at room temperature for 24 hours, and water (30 mL) was added thereto. The mixture was extracted with ethyl acetate (30 mL×2), washed with 1 mol/L aqueous sodium hydroxide (10 mL), dried over anhydrous magnesium sulfate, filtrated, and then concentrated. The residue was purified by preparative thin-layer column chromatography (dichloromethane/methanol) to give the title compound (40 mg).

$^1$H-NMR (300 MHz, DMSO-$d_6$) δ: 1.50-1.90 (6H, m), 2.01 (2H, t, J=11.3 Hz), 2.18-2.34 (2H, m), 2.50-2.58 (3H, m), 2.66 (2H, t, J=5.6 Hz), 3.15-3.27 (4H, m), 6.81 (1H, s), 7.73 (1H, d, J=7.6 Hz), 7.79 (1H, t, J=5.6 Hz), 7.85 (1H, d, J=8.1 Hz), 8.04 (1H, dd, J=7.9, 7.9 Hz).

Examples 13-15

According to the method of Example 12, Examples 13-15 were prepared from the corresponding Reference examples.

| Example | Chemical structure | Instrumental analyses data |
| --- | --- | --- |
| 13 | 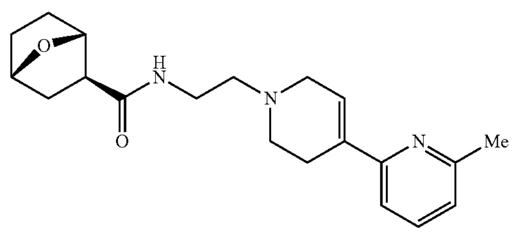 [SMILES: Cc1cccc(C2=CCN(CCNC(=O)[C@H]3C[C@@H]4CC[C@H]3O4)CC2)n1] | $^1$H-NMR (300 MHz, CDCl$_3$) δ: 1.40-1.57 (2H, m), 1.71-1.80 (2H, m), 1.85-1.93 (2H, m), 2.49-2.59 (4H, m), 2.59-2.72 (4H, m), 2.77 (2H, dd, J = 5.9, 4.5 Hz), 3.26 (2H, q, J = 2.9 Hz), 3.42 (2H, td, J = 6.2, 5.2 Hz), 4.58-4.75 (2H, m), 6.51 (1H, s), 6.62-6.71 (1H, m), 7.02 (1H, d, J = 7.6 Hz), 7.16 (1H, d, J = 7.8 Hz), 7.54 (1H, dd, J = 7.7, 7.7 Hz). |
| 14 | 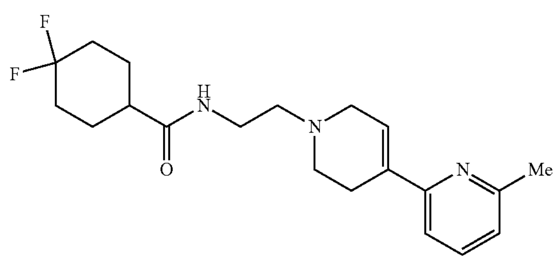 [SMILES: Cc1cccc(C2=CCN(CCNC(=O)C3CCC(F)(F)CC3)CC2)n1] | $^1$H-NMR (300 MHz, CDCl$_3$) δ: 1.62-2.02 (6H, m), 2.08-2.27 (3H, m), 2.57 (3H, s), 2.61-2.75 (4H, m), 2.80 (2H, t, J = 5.6 Hz), 3.27 (2H, d, J = 3.3 Hz), 3.45 (2H, q, J = 5.4 Hz), 6.31 (1H, s), 6.62-6.73 (1H, m), 7.04 (1H, d, J = 7.6 Hz), 7.17 (1H, d, J = 7.9 Hz), 7.56 (1H, dd, J = 7.7, 7.7 Hz). |
| 15 | 2HCl | $^1$H-NMR (300 MHz, CDCl$_3$) δ: 1.55-1.70 (1H, m), 1.70-1.90 (3H, m), 1.89-2.03 (4H, m), 2.08-2.25 2H, m), 2.39-2.50 (1H, m), 2.50-2.59 (5H, m), 2.72 (1H, tt, J = 11.9, 3.8 Hz), 2.93-3.10 (2H, m), 3.26-3.49 (2H, m), 3.59 (1H, ddd, J = 11.7, 8.9, 3.3 Hz), 3.70 (1H, dd, J = 11.5, 8.1 Hz), 3.82 (1H, td, J = 11.4, 4.4 Hz), 3.94 1H, dd, J = 11.5, 3.9 Hz), 6.56 (1H, s), 7.00 (2H, d, J = 7.7 Hz), 7.53 (1H, dd, J = 7.7, 7.7 Hz). |

Example 16

N-{2-[6-(Trifluoromethyl)-3',6'-dihydro[2,4'-bipyridin]-1'(2'H)-yl]ethyl}-tetrahydro-2H-pyran-3-carboxamide

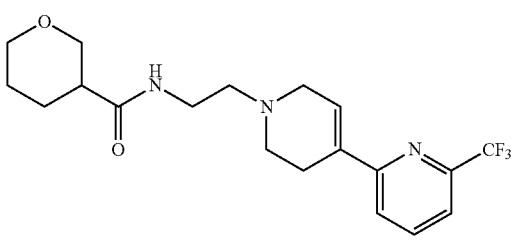 [SMILES: O=C(NCCN1CC=C(c2cccc(C(F)(F)F)n2)CC1)C1CCCOC1]

To a mixture of oxane-3-carboxylic acid (41.0 mg), triethylamine (0.263 mL), and acetonitrile (2.0 mL) was added 50% propylphosphonic acid anhydride/acetonitrile solution (301 mg) dropwise, and the mixture was stirred at room temperature for 10 minutes. The compound of Reference example 7 (144 mg) was added thereto, and the reaction mixture was stirred at room temperature for 24 hours. The solvent was removed from the reaction mixture, and water (30 mL) was added to the residue. The mixture was extracted with ethyl acetate (30 mL×2), washed with aqueous saturated sodium bicarbonate (30 mL), dried over anhydrous sodium sulfate, filtrated, and then concentrated. The residue was purified by preparative thin-layer column chromatography (dichloromethane/methanol) to give the title compound (22.0 mg).

$^1$H-NMR (300 MHz, CDCl$_3$) δ: 1.44-1.78 (4H, m), 1.81-2.00 (2H, m), 2.37-2.49 (1H, m), 2.63-2.83 (4H, m), 3.28 (2H, q, J=2.9 Hz), 3.39-3.50 (2H, m), 3.55 (1H, ddd, J=11.3, 9.1, 3.3 Hz), 3.68 (1H, dd, J=11.5, 8.2 Hz), 3.80 (1H, td, J=11.4, 4.4 Hz), 3.92 (1H, dd, J=11.7, 3.8 Hz), 6.47 (1H, s), 6.80 (1H, tt, J=3.6, 1.5 Hz), 7.45-7.62 (2H, m), 7.76-7.89 (1H, m).

Examples 17-28

According to the method of Example 16, Examples 17-28 were prepared from the corresponding Reference examples.

| Example | Chemical structure | Instrumental analyses data |
|---|---|---|
| 17 | 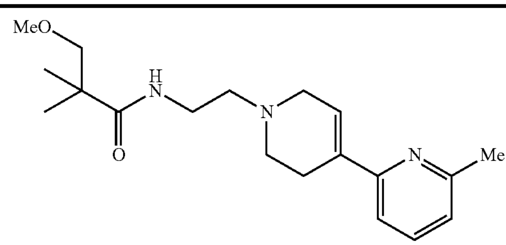 | $^1$H-NMR (300 MHz, CDCl$_3$) δ: 1.17 (6H, s), 2.56 (3H, s), 2.59-2.71 (4H, m), 2.72-2.81 (2H, m), 3.26 (2H, q, J = 2.9 Hz), 3.33 (2H, s), 3.35 (3H, s), 3.42 (2H, td, J = 6.2, 4.9 Hz), 6.69 (1H, tt, J = 3.6, 1.6 Hz), 7.02 (1H, d, J = 7.6 Hz), 7.16 (2H, d, J = 7.8 Hz), 7.54 (1H, dd, J = 7.7, 7.7 Hz). |
| 18 | HCO$_2$H | $^1$H-NMR (300 MHz, CDCl$_3$) δ: 1.19 (6H, s), 2.86-2.94 (2H, m), 3.01 (2H, t, J = 6.1 Hz), 3.16 (2H, t, J = 5.9 Hz), 3.36 (2H, s), 3.37 (3H, s), 3.50-3.72 (4H, m), 6.68-6.78 (1H, m), 7.47 (1H, s), 7.59 (2H, dd, J = 7.9, 5.5 Hz), 7.86 (1H, dd, J = 7.9, 7.9 Hz), 8.34 (1H, s). |
| 19 | 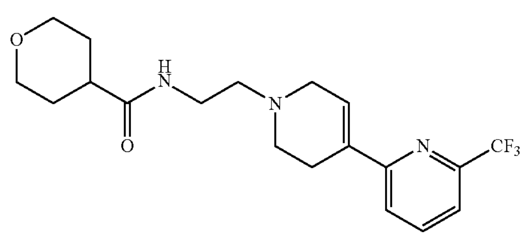 [SMILES: O=C(NCCN1CC=C(c2cccc(C(F)(F)F)n2)CC1)C1CCOCC1] | $^1$H-NMR (300 MHz, CDCl$_3$) δ: 1.71-1.92 (4H, m), 2.27-2.43 (1H, m), 2.61-2.82 (6H, m), 3.27 (2H, q, J = 2.9 Hz), 3.33-3.52 (4H, m), 3.93-4.09 (2H, m), 6.15 (1H, s), 6.80 (1H, td, J = 3.5, 1.7 Hz), 7.56 (2H, dd, J = 10.7, 7.9 Hz), 7.84 (1H, dd, J = 7.9, 7.9 Hz). |
| 20 | 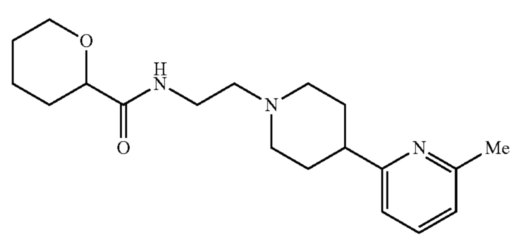 [SMILES: Cc1cccc(C2CCN(CCNC(=O)C3CCCCO3)CC2)n1] | $^1$H-NMR (300 MHz, CDCl$_3$) δ: 1.33-1.49 (1H, m), 1.51-1.67 (3H, m), 1.78-2.02 (5H, m), 2.08-2.22 (3H, m), 2.48-2.60 (5H, m), 2.71 (1H, tt, J = 12.0, 3.9 Hz), 3.05 (2H, td, J = 11.5, 3.2 Hz), 3.33-3.46 (2H, m), 3.51 (1H, td, J = 11.2, 3.4 Hz), 3.80 (1H, dd, J = 11.2, 2.5 Hz), 4.03-4.13 (1H, m), 6.94 (1H, s), 7.00 (2H, dd, J = 7.6, 1.9 Hz), 7.53 (1H, dd, J = 7.7, 7.7 Hz). |

-continued

| Example | Chemical structure | Instrumental analyses data |
|---|---|---|
| 21 | 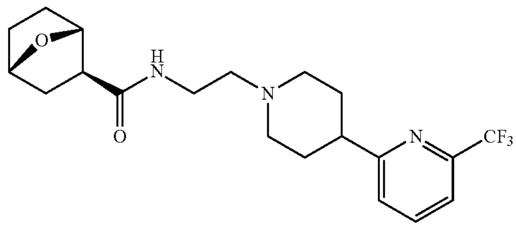 [SMILES: O=C(NCCN1CCC(c2cccc(C(F)(F)F)n2)CC1)[C@H]1C[C@@H]2CC[C@H]1O2] | ¹H-NMR (300 MHz, CDCl₃) δ: 1.41-1.58 (2H, m), 1.71-1.83 (2H, m), 1.83-1.95 (4H, m), 1.99 (2H, d, J = 13.2 Hz), 2.09-2.27 (2H, m), 2.43-2.65 (3H, m), 2.83 (1H, tt, J = 11.7, 4.0 Hz), 2.94-3.11 (2H, m), 3.37 (2H, q, J = 6.0 Hz), 4.62-4.78 (2H, m), 6.58 (1H, s), 7.39 (1H, d, J = 7.9 Hz), 7.53 (1H, dd, J = 7.7, 0.9 Hz), 7.81 (1H, dd, J = 7.8, 7.8 Hz). |
| 22 | 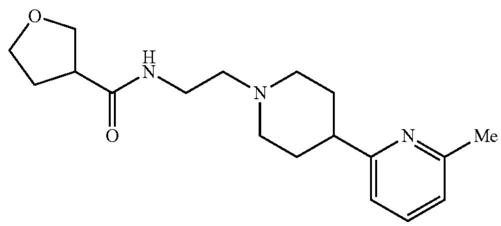 [SMILES: Cc1cccc(C2CCN(CCNC(=O)C3CCOC3)CC2)n1] | ¹H-NMR (300 MHz, CDCl₃) δ: 1.83 (2H, qd, J = 12.4, 3.8 Hz), 1.93-2.02 (2H, m), 2.08-2.25 (4H, m), 2.47-2.60 (5H, m), 2.71 (1H, tt, J = 11.9, 3.9 Hz), 2.88-2.98 (1H, m), 3.00-3.07 (2H, m), 3.40 (2H, q, J = 5.6 Hz), 3.79-4.04 (4H, m), 6.39 (1H, s), 6.99 (2H, dd, J = 7.8, 2.4 Hz), 7.53 (1H, dd, J = 7.7, 7.7 Hz). |
| 23 | 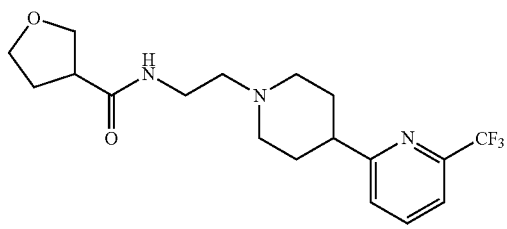 [SMILES: O=C(NCCN1CCC(c2cccc(C(F)(F)F)n2)CC1)C1CCOC1] | ¹H-NMR (300 MHz, CDCl₃) δ: 1.83-2.07 (4H, m), 2.14-2.30 (4H, m), 2.56-2.63 (2H, m), 2.79-2.90 (1H, m), 2.91-3.03 (1H, m), 3.03-3.10 (2H, m), 3.42 (2H, q, J = 5.6 Hz), 3.80-4.07 (4H, m), 6.32 (1H, s), 7.40 (1H, d, J = 7.9 Hz), 7.54 (1H, dd, J = 7.7, 0.9 Hz), 7.82 (1H, dd, J = 7.8, 7.8 Hz). |
| 24 | 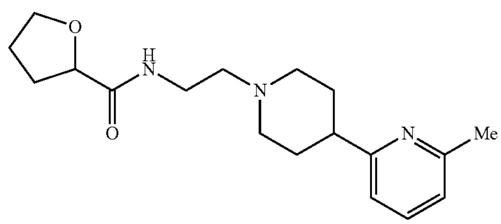 [SMILES: Cc1cccc(C2CCN(CCNC(=O)C3CCCO3)CC2)n1] | ¹H-NMR (300 MHz, CDCl₃) δ: 1.74-1.91 (3H, m), 1.91-2.04 (3H, m), 2.04-2.23 (3H, m), 2.30 (1H, dd, J = 12.7, 7.7 Hz), 2.46-2.62 (5H, m), 2.71 (1H, tt, J = 12.1, 3.7 Hz), 2.95-3.08 (2H, m), 3.41 (2H, q, J = 6.0 Hz), 3.87-4.04 (2H, m), 4.39 (1H, dd, J = 8.4, 5.5 Hz), 7.00 (2H, d, J = 7.7 Hz), 7.12 (1H, s), 7.53 (1H, dd, J = 7.7, 7.7 Hz). |
| 25 | 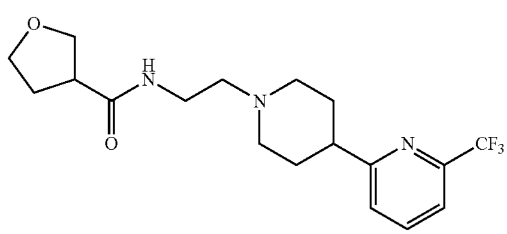 [SMILES: O=C(NCCN1CCC(c2cccc(C(F)(F)F)n2)CC1)C1CCOC1] | ¹H-NMR (300 MHz, CDCl₃) δ: 1.79-2.03 (6H, m), 2.06-2.38 (4H, m), 2.57 (2H, dd, J = 6.3, 1.6 Hz), 2.84 (1H, tt J = 11.8, 4.1 Hz), 2.96-3.10 (2H, m), 3.41 (2H, q, J = 6.0 Hz), 3.83-4.06 (2H, m), 4.39 (1H, dd, J = 8.4, 5.5 Hz), 7.12 (1H, s), 7.39 (1H, d, J = 7.9 Hz), 7.53 (1H, dd, J = 7.8, 0.9 Hz), 7.81 (1H, dd, J = 7.8, 7.8 Hz). |
| 26 | 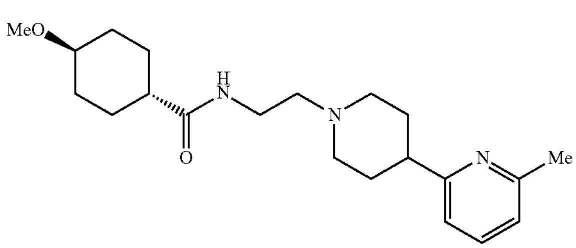 [SMILES: CO[C@H]1CC[C@H](C(=O)NCCN2CCC(c3cccc(C)n3)CC2)CC1] | ¹H-NMR (300 MHz, DMSO-d₆) δ: 1.00-1.15 (2H, m), 1.30-1.47 (2H, m), 1.63-1.83 (5H, m), 1.96-2.10 (5H, m), 2.35 (2H, t, J = 6.9 Hz), 2.43 (3H, s), 2.55-2.62 (2H, m), 2.94 (2H, d, J = 11.2 Hz), 3.01-3.10 (1H, m), 3.16 (2H, q, J = 6.5 Hz), 3.23 (3H, s), 7.04 (2H, dd, J = 7.6, 2.5 Hz), 7.58 (1H, dd, J = 7.7, |

| Example | Chemical structure | Instrumental analyses data |
|---|---|---|
| | | 7.7 Hz), 7.64 (1H, d, J = 5.6 Hz). |
| 27 | MeO—[cyclohexyl]—C(=O)NH—CH2CH2—N[piperidine]—[pyridine]—CF3 | $^1$H-NMR (300 MHz, DMSO-$d_6$) δ: 1.09 (2H, t, J = 12.3 Hz), 1.37 (2H, d, J = 13.0 Hz), 1.68-1.86 (5H, m), 1.95-2.11 (5H, m), 2.30-2.39 (2H, m), 2.70-2.80 (1H, m), 2.92-3.01 (2H, m), 3.06 (1H, s), 3.13-3.19 (1H, m), 3.23 (3H, s), 7.58-7.69 (2H, m), 7.72 (1H, d, J = 7.7 Hz), 8.02 (1H, dd, J = 7.8, 7.8 Hz). |
| 28 | [tetrahydropyran]—C(=O)NH—CH2CH2—N[piperidine]—[pyridine]—OCF3 | $^1$H-NMR (300 MHz, DMSO-$d_6$) δ: 1.49-1.63 (4H, m), 1.78 (4H, s), 2.04 (2H, s), 2.36 (3H, d, J = 2.9 Hz), 2.57-2.72 (1H, m), 2.94 (2H, d, J = 11.0 Hz), 3.11-3.31 (4H, m), 3.85 (2H, td, J = 11.2, 3.4 Hz), 7.09 (1H, d, J = 8.0 Hz), 7.32 (1H, d, J = 7.6 Hz), 7.71 (1H, s), 7.93 (1H, dd, J = 7.8, 7.8 Hz). |

Example 29

N-[2-(6-Methyl-3',6'-dihydro[2,4'-bipyridin]-1'(2'H)-yl)ethyl]-tetrahydro-2H-pyran-4-carboxamide

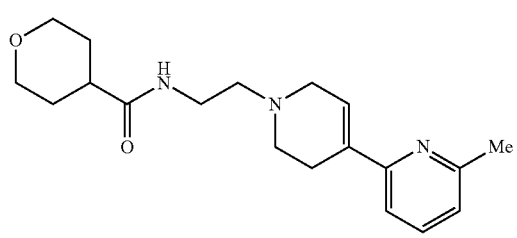 [SMILES: Cc1cccc(C2=CCN(CCNC(=O)C3CCOCC3)CC2)n1]

To a mixture of the compound of Reference example 8 (150 mg), sodium bicarbonate (231 mg), and dichloromethane (5.0 mL) was slowly added tetrahydro-2H-pyran-4-carbonylchloride (81.8 mg) under ice temperature. The mixture was stirred at room temperature for 20 hours, and 10% aqueous potassium carbonate (30 mL) was added thereto. The mixture was stirred at room temperature for 15 minutes. The organic layer was separated, washed with brine, dried over anhydrous magnesium sulfate, filtrated, and then concentrated. The residue was purified by preparative thin-layer column chromatography (chloroform/3 mol/L ammonia/methanol) to give the title compound (99.0 mg).

$^1$H-NMR (300 MHz, CDCl$_3$) δ: 1.71-1.90 (4H, m), 2.30-2.43 (1H, m), 2.57 (3H, s), 2.64-2.75 (4H, m), 2.75-2.83 (2H, m), 3.23-3.31 (2H, m), 3.37-3.52 (4H, m), 3.98-4.08 (2H, m), 6.27 (1H, s), 6.63-6.71 (1H, m), 7.04 (1H, d, J=7.6 Hz), 7.17 (1H, d, J=7.8 Hz), 7.56 (1H, dd, J=7.7, 7.7 Hz).

Example 30

2,2-Dimethyl-N-[2-(6-methyl-3',6'-dihydro[2,4'-bipyridin]-1'(2'H)-yl)ethyl]propanamide

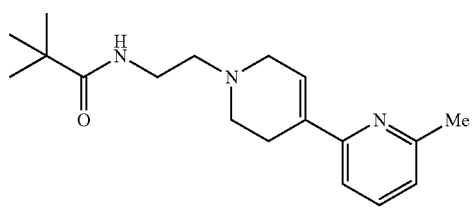 [SMILES: Cc1cccc(C2=CCN(CCNC(=O)C(C)(C)C)CC2)n1]

According to the method of Example 29, the title compound (48 mg) was prepared from Reference example 8 (150 mg).

$^1$H-NMR (300 MHz, DMSO-$d_6$) δ: 1.08 (9H, s), 2.45 (3H, s), 2.47-2.54 (4H, m), 2.65 (2H, t, J=5.6 Hz), 3.13-3.18 (2H, m), 3.19-3.26 (2H, m), 6.58-6.72 (1H, m), 7.09 (1H, d, J=7.6 Hz), 7.29 (1H, d, J=7.9 Hz), 7.38 (1H, dd, J=5.6, 5.6 Hz), 7.63 (1H, dd, J=7.7, 7.7 Hz).

Example 31

2,2-Dimethyl-N-{2-[6-(trifluoromethyl)-3',6'-dihydro[2,4'-bipyridin]-1'(2'H)-yl]ethyl}propanamide

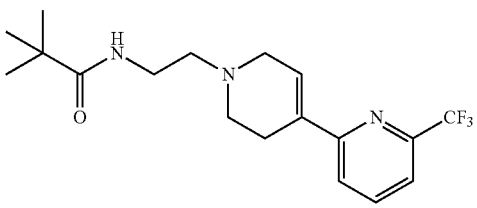 [SMILES: CC(C)(C)C(=O)NCCN1CC=C(c2cccc(C(F)(F)F)n2)CC1]

To a mixture of the compound of Reference example 7 (160 mg), triethylamine (0.319 mL), and dichloromethane (2.0 mL) was slowly added pivaloyl chloride (46.0 mg). The reaction mixture was stirred at room temperature for 20 hours, and then water (30 mL) was added thereto. The mixture was extracted with ethyl acetate (30 mL×2), washed with brine (30 mL), dried over anhydrous sodium sulfate, filtrated, and then concentrated. The residue was purified by preparative HPLC to give the title compound (23 mg) as its formate.

$^1$H-NMR (300 MHz, CDCl$_3$) δ: 1.23 (9H, s), 2.84-2.97 (2H, m), 3.05-3.13 (2H, m), 3.18 (2H, t, J=5.7 Hz), 3.58-3.64 (2H, m), 3.66-3.70 (2H, m), 6.75 (1H, s), 6.92 (1H, s), 7.61 (2H, dd, J=10.5, 7.8 Hz), 7.88 (1H, dd, J=7.9, 7.9 Hz).

Examples 32-34

According to the method of Example 31, Examples 32-34 were prepared from the corresponding Reference examples.

Example 35

N-{2-[4-(6-Cyanopyridin-2-yl)piperidin-1-yl]ethyl}-tetrahydro-2H-pyran-4-carboxamide

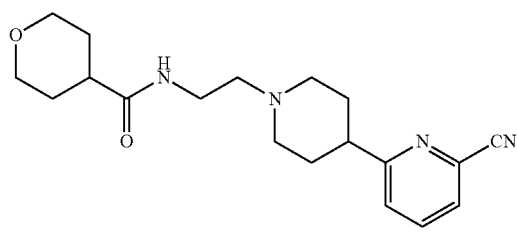

A mixture of the compound of Example 32 (180 mg), sodium cyanide (500 mg), and dimethylsulfoxide (10 mL) was stirred at 150° C. for 72 hours, and then water (100 mL) was added thereto. The mixture was extracted with ethyl acetate (100 mL×2), washed with aqueous saturated sodium bicarbonate, dried over anhydrous magnesium sulfate, filtrated, and then concentrated. The residue was purified by preparative thin-layer column chromatography (dichloromethane/3 mol/L ammonia/methanol) to give the title

| Example | Chemical structure | Instrumental analyses data |
| --- | --- | --- |
| 32 | 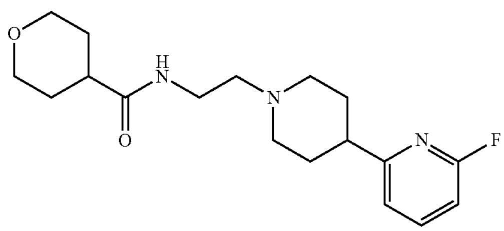 [SMILES: O=C(NCCN1CCC(c2cccc(F)n2)CC1)C1CCOCC1] | $^1$H-NMR (300 MHz, CDCl$_3$) δ: 1.74-1.99 (8H, m), 2.14 (2H, td, J = 11.6, 2.8 Hz), 2.39 (1H, tt, J = 10.5, 4.9 Hz), 2.53 (2H, t, J = 5.9 Hz), 2.69 (1H, tt, J = 11.5, 4.2 Hz), 3.01 (2H, td, J = 11.9, 3.2 Hz), 3.34-3.53 (4H, m), 3.98-4.11 (2H, m), 6.20 (1H, s), 6.79 (1H, dd, J = 8.1, 2.9 Hz), 7.07 (1H, dd, J = 7.4, 2.5 Hz), 7.74 (1H, dd, J = 8.0, 8.0 Hz). |
| 33 | 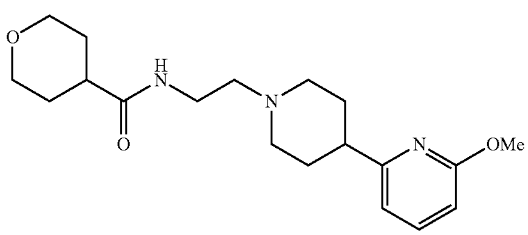 [SMILES: COc1cccc(C2CCN(CCNC(=O)C3CCOCC3)CC2)n1] | $^1$H-NMR (300 MHz, DMSO-d$_6$) δ: 1.53-1.62 (4H, m), 1.67-1.87 (4H, m), 2.05 (2H, s), 2.30-2.41 (3H, m), 2.54-2.60 (1H m), 2.94-3.00 (2H, m) 3.16-3.23 (2H, m), 3.29 (2H, tt, J = 7.9, 3.8 Hz), 3.80-3.89 (5H, m), 6.61 (1H, dd, J = 8.2, 0.7 Hz), 6.83 (1H, d, J = 7.2 Hz), 7.60 (1H, dd, J = 8.2, 7.3 Hz), 7.71 (1H, s). |
| 34 | | $^1$H-NMR (300 MHz, CDCl$_3$) δ: 1.73-2.10 (8H, m), 2.11-2.29 (2H, m), 2.34-2.46 (1H, m), 2.52-2.66 (2H, m), 2.73-2.87 (1H, m), 3.00-3.10 (2H, m), 3.34-3.59 (4H, m), 4.01-4.11 (2H, m), 6.62 (1H, t, J = 55.6 Hz), 7.33 (1H, s), 7.50 (1H, d, J = 7.7 Hz), 7.80 (1H, dd, J = 7.8, 7.8 Hz). | compound (11.0 mg). ¹H-NMR (300 MHz, DMSO-d₆) δ: 1.52-1.60 (4H, m), 1.62-1.87 (4H, m), 1.94-2.17 (2H, m), 2.25-2.43 (3H, m), 2.66-2.80 (1H, m), 2.96 (2H, d, J=10.9 Hz), 3.09-3.31 (4H, m), 3.85 (2H, td, J=11.2, 3.4 Hz), 7.67 (2H, dd, J=8.0, 1.1 Hz), 7.87 (1H, dd, J=7.7, 1.1 Hz), 7.98 (1H, dd, J=7.8, 7.8 Hz).

Example 36

N-{2-[4-(6-Aminopyridin-2-yl)piperidin-1-yl]ethyl}-tetrahydro-2H-pyran-4-carboxamide

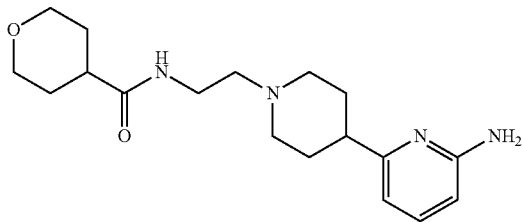 [SMILES: Nc1cccc(C2CCN(CCNC(=O)C3CCOCC3)CC2)n1]

A mixture of the compound of Reference example 15 (270 mg), 50% Raney nickel/water-suspension (0.2 mL), and methanol (5.0 mL) was stirred under hydrogen atmosphere at room temperature for 24 hours. The reaction mixture was filtrated on Celite, and washed with methanol (10 mL×2). The filtrate was concentrated. The residue was triturated with a mixture of dichloromethane and diethyl ether to give the title compound (22 mg).
¹H-NMR (300 MHz, DMSO-d₆) δ: 1.49-1.61 (4H, m), 1.62-1.77 (4H, m), 1.99 (2H, td, J=11.3, 3.0 Hz), 2.25-2.42 (4H, m), 2.87-2.98 (2H, m), 3.17 (2H, q, J=6.5 Hz), 3.23-3.32 (2H, m), 3.85 (2H, td, J=11.2, 3.4 Hz), 5.72 (2H, s), 6.25 (1H, d, J=8.1 Hz), 6.34 (1H, d, J=7.3 Hz), 7.27 (1H, dd, J=7.7, 7.7 Hz), 7.68 (1H, J=5.6, 5.6 Hz).

Example 37

N-(2-{4-[6-(Methylamino)pyridin-2-yl]piperidin-1-yl}ethyl)-tetrahydro-2H-pyran-4-carboxamide

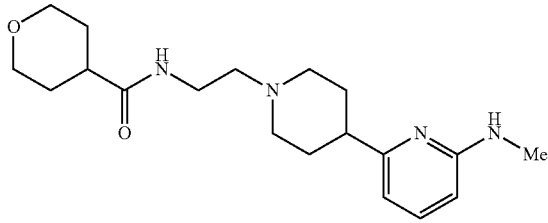 [SMILES: CNc1cccc(C2CCN(CCNC(=O)C3CCOCC3)CC2)n1]

To a solution of the compound of Example 36 (100 mg) in methanol (1.0 mL) were added paraformaldehyde (36.0 mg) and sodium methoxide (81.0 mg). The reaction mixture was refluxed for 2 hours. The reaction mixture was cooled under ice temperature, sodium borohydride (46.0 mg) was added to the cooled reaction mixture, and then the mixture was refluxed for 2 hours. To the reaction mixture was added aqueous saturated sodium bicarbonate (5.0 mL). The mixture was extracted with ethyl acetate (30 mL×2), dried over anhydrous magnesium sulfate, filtrated, and then concentrated. The residue was purified by preparative thin-layer column chromatography (dichloromethane/3 mol/L ammonia/methanol) to give the title compound (36.0 mg).
¹H-NMR (300 MHz, CDCl₃) δ: 1.68-1.89 (6H, m), 1.89-2.01 (2H, m), 2.04-2.22 (2H, m), 2.39 (1H, tt, J=10.4, 5.3 Hz), 2.46-2.60 (3H, m), 2.92 (3H, d, J-5.1 Hz), 2.95-3.07 (2H, m), 3.29-3.54 (4H, m), 4.05 (2H, td, J=11.5, 3.6 Hz), 4.36-4.62 (1H, m), 6.25 (2H, d, J=8.2 Hz), 6.49 (1H, d, J=7.3 Hz), 7.43 (1H, dd, J=8.2, 7.4 Hz).

Example 38

N-(2-{4-[6-(Dimethylamino)pyridin-2-yl]piperidin-1-yl}ethyl)-tetrahydro-2H-pyran-4-carboxamide

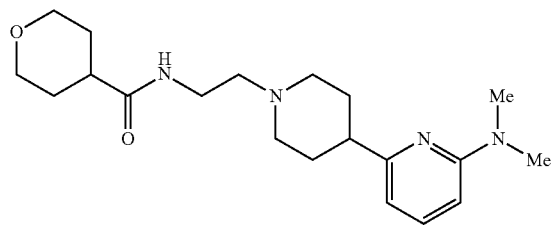 [SMILES: CN(C)c1cccc(C2CCN(CCNC(=O)C3CCOCC3)CC2)n1]

To a solution of the compound of Example 36 (50.0 mg) in dichloroethane (1.5 mL) was added paraformaldehyde (18.0 mg), and the reaction mixture was stirred at room temperature for 1 hour. Sodium cyanoborohydride (23.9 mg) was added thereto, and the reaction mixture was stirred at room temperature for 24 hours. To the reaction mixture was added dichloromethane (30 mL). The mixture was washed with aqueous saturated sodium bicarbonate (10 mL×2), dried over anhydrous sodium sulfate, filtrated, and then concentrated. The residue was purified by preparative thin-layer column chromatography (dichloromethane/3 mol/L ammonia/methanol) to give the title compound (36.0 mg).
¹H-NMR (300 MHz, CDCl₃) δ: 1.75-2.02 (8H, m), 2.15 (2H, t, J=11.5 Hz), 2.32-2.46 (1H, m), 2.48-2.64 (3H, m), 3.00 (2H, d, J=11.3 Hz), 3.10 (6H, s), 3.33-3.53 (4H, m), 4.04 (2H, td, J=11.4, 3.4 Hz), 6.28 (1H, s), 6.37 (1H, d, J=8.6 Hz), 6.44 (1H, d, J=7.3 Hz), 7.40 (1H, dd, J=8.4, 7.3 Hz).

Reference Example 1

6-(Trifluoromethyl)-1',2',3',6'-tetrahydro-2,4'-bipyridine

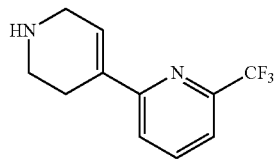 [SMILES: FC(F)(F)c1cccc(C2=CCNCC2)n1]

To a mixture of N-Boc-1,2,3,6-tetrahydro-4-(4,4,5,5-tetramethyl-[1,3,2]-dioxaborolan-2-yl)-pyridine (41.0 g), dimethoxyethane (221 mL), and water (111 mL) were added 2-bromo-6-(trifluoromethyl)pyridine (30.0 g), sodium carbonate (70.3 g), and tetrakis(triphenylphosphine)palladium (0) (7.67 g). The reaction mixture was stirred at 80° C. for 15 hours, and then concentrated hydrochloric acid (300 mL) was slowly added dropwise thereto. The reaction mixture was stirred at room temperature for 1 hour, and then filtrated on Celite. The filtrate was washed with chloroform. To the aqueous layer was added 20% aqueous sodium hydroxide (375 mL), and extracted with chloroform. The organic layer was dried over sodium sulfate, filtrated, and then concentrated in vacuo to give the title compound (26.9 g).

$^1$H-NMR (400 MHz, CDCl$_3$) δ: 2.53-2.59 (2H, m), 3.11 (2H, t, J=5.7 Hz), 3.59 (2H, q, J=3.0 Hz), 6.81-6.84 (1H, m), 7.48 (1H, d, J=7.8 Hz), 7.51 (1H, d, J=8.0 Hz), 7.78 (1H, dd, J=7.9, 7.9 Hz).

Reference Example 2

2-(Piperidin-4-yl)-6-(trifluoromethyl)pyridine

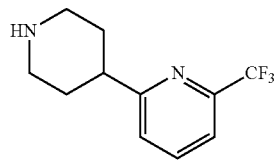 [SMILES: FC(F)(F)c1cccc(C2CCNCC2)n1]

To a solution of the compound of Reference example 1 (53.8 g) in methanol (236 mL) was added 10% palladium/carbon (12.5 g), and the reaction mixture was stirred under hydrogen atmosphere at room temperature for 15 hours. The reaction mixture was filtrated on Celite, and the filtrate was concentrated in vacuo to give the title compound (54.1 g).

$^1$H-NMR (400 MHz, CDCl$_3$) δ: 1.73-1.85 (2H, m), 1.95-2.02 (2H, m), 2.76-2.85 (2H, m), 2.90-2.99 (1H, m), 3.23-3.30 (2H, m), 7.36 (1H, d, J=7.8 Hz), 7.49 (1H, d, J=7.8 Hz), 7.78 (1H, dd, J=7.8, 7.8 Hz).

Reference Example 3 tert-Butyl (2-{4-[6-(trifluoromethyl)pyridin-2-yl]piperidin-1-yl}ethyl)carbamate

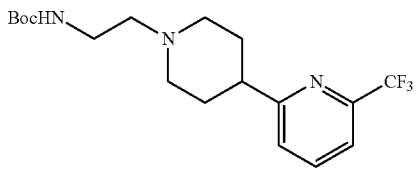 [SMILES: CC(C)(C)OC(=O)NCCN1CCC(c2cccc(C(F)(F)F)n2)CC1]

To a mixture of the compound of Reference example 2 (9.62 g), tetrabutylammonium bromide (1.35 g), 50% aqueous potassium carbonate (57.7 g), and THF (84 mL) was added tert-butyl (2-bromoethyl)carbamate (9.83 g). The reaction mixture was stirred at 70° C. for 15 hours, water was added thereto, and the mixture was extracted with ethyl acetate. The organic layer was dried over sodium sulfate, filtrated, and concentrated in vacuo. The residue was purified by silica gel column chromatography (chloroform/methanol) to give the title compound (11.0 g).

$^1$H-NMR (400 MHz, CDCl$_3$) δ: 1.44 (9H, s), 1.76-1.97 (4H, m), 2.05-2.14 (2H, m), 2.47 (2H, t, J=6.0 Hz), 2.73-2.84 (1H, m), 2.95-3.03 (2H, m), 3.17-3.28 (2H, m), 5.01 (1H, brs), 7.35 (1H, d, J=7.8 Hz), 7.49 (1H, d, J=7.8 Hz), 7.77 (1H, dd, J=7.8, 7.8 Hz).

Reference Example 4

2-{4-[6-(Trifluoromethyl)pyridin-2-yl]piperidin-1-yl}ethylamine trihydrochloride

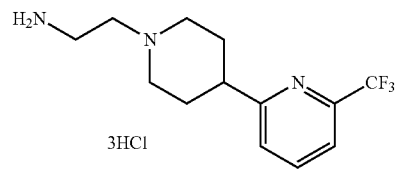 [SMILES: NCCN1CCC(c2cccc(C(F)(F)F)n2)CC1]

To a solution of the compound of Reference example 3 (1.57 g) in dichloromethane (8.4 mL) was added 4 mol/L hydrochloric acid/ethyl acetate (10.5 mL). The reaction mixture was stirred at room temperature for 4 hours, and the solvent was removed. The residue was stirred in diethyl ether and filtrated to give the title compound (1.37 g).

$^1$H-NMR (400 MHz, DMSO-D$_6$) δ: 2.06-2.17 (4H, m), 3.07-3.22 (3H, m), 3.27-3.45 (4H, m), 3.63-3.71 (2H, m), 7.65 (1H, d, J=7.8 Hz), 7.78 (1H, d, J=7.8 Hz), 8.08 (1H, dd, J=7.8, 7.8 Hz), 8.43 (3H, brs).

Reference Example 5

6-Methyl-1',2',3',6'-tetrahydro-2,4'-bipyridine

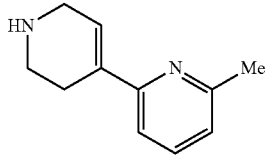 [SMILES: Cc1cccc(C2=CCNCC2)n1]

To a mixture of 2-bromo-6-methylpyridine (5.11 g), dimethoxyethane (79 mL), and water (20 mL) were added N-Boc-1,2,3,6-tetrahydro-4-(4,4,5,5-tetramethyl-[1,3,2]-dioxaborolan-2-yl)-pyridine (11.0 g), potassium carbonate (8.21 g), and tetrakis(triphenylphosphine)palladium(0) (3.43 g). The reaction mixture was stirred at 80° C. for 4 hours, water was added thereto, and the mixture was extracted with ethyl acetate. The organic layer was dried over sodium sulfate, filtrated, and concentrated in vacuo. The residue was purified by silica gel column chromatography (hexane/ethyl acetate).

To a solution of the purified product in ethyl acetate (20 mL) was added 4 mol/L hydrochloric acid/ethyl acetate (20 mL). The reaction mixture was stirred at room temperature for 24 hours, and then concentrated. To the residue was added aqueous saturated sodium bicarbonate, and the mixture was extracted with chloroform/methanol solution. The organic layer was dried over sodium sulfate, filtrated, and concentrated in vacuo. The residue was purified by amino silica gel column chromatography (chloroform/methanol) to give the title compound (4.88 g).

$^1$H-NMR (400 MHz, CDCl$_3$) δ: 2.51-2.57 (5H, m), 3.12 (2H, t, J=5.7 Hz), 3.58 (2H, q, J=3.1 Hz), 6.70-6.74 (1H, m), 7.00 (1H, d, J=7.8 Hz), 7.13 (1H, d, J=7.8 Hz), 7.53 (1H, dd, J=7.8, 7.8 Hz).

Reference Example 6

2-[4-(6-Methylpyridin-2-yl)piperidin-1-yl]ethylamine trihydrochloride

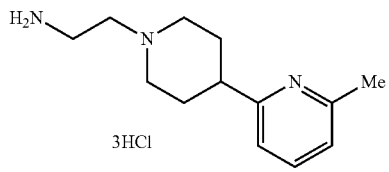 [SMILES: Cc1cccc(C2CCN(CCN)CC2)n1]

According to the method of Reference examples 2-4, the title compound was prepared from Reference example 5.

$^1$H-NMR (300 MHz, DMSO-D$_6$) δ: 2.11-2.35 (4H, m), 2.78 (3H, s), 3.13-3.29 (2H, m), 3.31-3.46 (4H, m), 3.47-3.61 (1H, m), 3.66-3.78 (2H, m), 7.65 (1H, d, J=8.1 Hz), 7.77 (1H, d, J=7.5 Hz), 8.41 (1H, dd, J=7.8, 7.8 Hz), 8.47 (3H, brs), 11.30 (1H, brs).

Reference Example 7

2-[6-(Trifluoromethyl)-3',6'-dihydro[2,4'-bipyridin]-1'(2'H)-yl]ethylamine trihydrochloride

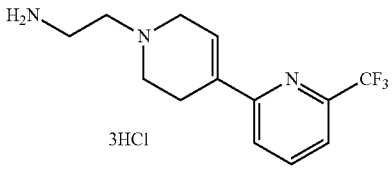 [SMILES: NCCN1CC=C(c2cccc(C(F)(F)F)n2)CC1]

According to the method of Reference examples 3-4, the title compound was prepared from Reference example 1.

$^1$H-NMR (300 MHz, D$_2$O) δ: 2.84-3.02 (2H, m), 3.44-3.55 (2H, m), 3.56-3.69 (4H, m), 3.99-4.10 (2H, m), 6.50-6.59 (1H, m), 7.72 (1H, d, J=3.7 Hz), 7.75 (1H, d, J=3.3 Hz), 8.00 (1H, dd, J=7.9, 7.9 Hz).

Reference Example 8

2-(6-Methyl-3',6'-dihydro[2,4'-bipyridin]-1'(2'H)-yl)ethylamine trihydrochloride

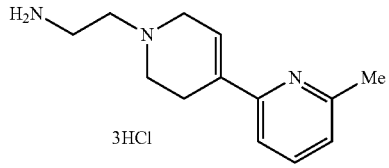 [SMILES: Cc1cccc(C2=CCN(CCN)CC2)n1]

According to the method of Reference examples 3-4, the title compound was prepared from Reference example 5.

$^1$H-NMR (300 MHz, DMSO-d$_6$) δ: 2.68 (3H, s), 2.95-3.07 (2H, m), 3.33-3.45 (3H, m), 3.48-3.56 (2H, m), 3.70-3.84 (1H, m), 3.94-4.07 (1H, m), 4.12-4.27 (1H, m), 6.83 (1H, d, J=3.9 Hz), 7.55 (1H, d, J=7.8 Hz), 7.69 (1H, d, J=8.0 Hz), 8.12 (1H, dd, J=8.2, 8.2 Hz), 8.60 (3H, s), 11.64 (1H, s).

Reference Example 9 tert-Butyl {2-[6-(trifluoromethoxy)-3',6'-dihydro[2,4'-bipyridin]-1'(2'H)-yl]ethyl}carbamate

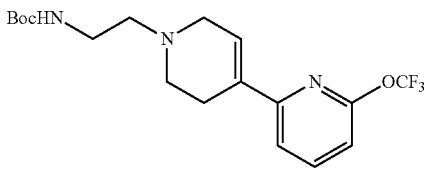 [SMILES: CC(C)(C)OC(=O)NCCN1CC=C(c2cccc(OC(F)(F)F)n2)CC1]

According to the method of Reference examples 1 and 3, the title compound was prepared from 2-chloro-6-trifluoromethoxypyridine.

$^1$H-NMR (300 MHz, CDCl$_3$) δ: 1.47 (9H, s), 2.58-2.70 (4H, m), 2.71-2.79 (2H, m), 3.20-3.28 (2H, m), 3.28-3.36 (2H, m), 6.73-6.82 (1H, m), 6.85 (1H, d, J=8.0 Hz), 7.23-7.30 (1H, m), 7.74 (1H, dd, J=7.9, 7.9 Hz).

Reference Example 10 tert-Butyl (2-{4-[6-(trifluoromethoxy)pyridin-2-yl]piperidin-1-yl}ethyl)carbamate

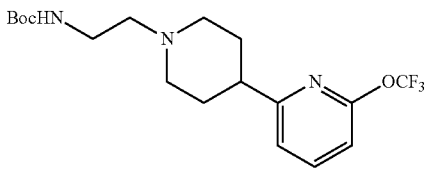 [SMILES: CC(C)(C)OC(=O)NCCN1CCC(c2cccc(OC(F)(F)F)n2)CC1]

According to the method of Reference example 2, the title compound was prepared from Reference example 9.

$^1$H-NMR (300 MHz, CDCl$_3$) δ: 1.47 (9H, s), 1.82-2.07 (4H, m), 2.18-2.30 (2H, m), 2.49-2.62 (2H, m), 2.66-2.79 (1H, m), 3.10 (2H, d, J=11.2 Hz), 3.24-3.40 (2H, m), 6.87 (1H, d, J=8.1 Hz), 7.11 (1H, d, J=7.5 Hz), 7.73 (1H, dd, J=7.8, 7.8 Hz).

Reference Example 11

2-{4-[6-(Trifluoromethoxy)pyridin-2-yl]piperidin-1-yl}ethylamine trihydrochloride

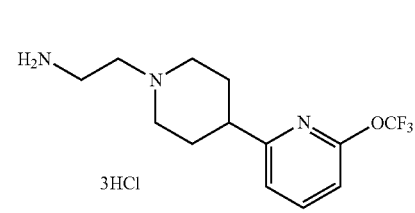 [SMILES: NCCN1CCC(c2cccc(OC(F)(F)F)n2)CC1]

According to the method of Reference example 4, the title compound was prepared from Reference example 10.

$^1$H-NMR (300 MHz, D$_2$O) δ: 1.93-2.14 (2H, m), 2.15-2.26 (2H, m), 3.04-3.13 (1H, m), 3.16-3.33 (2H, m), 3.38-3.54 (4H, m), 3.62-3.77 (2H, m), 7.13 (1H, d, J=8.2 Hz), 7.31 (1H, d, J=7.6 Hz), 7.91 (1H, dd, J=7.9, 7.9 Hz).

Reference Example 12

2-[4-(6-Fluoropyridin-2-yl)piperidin-1-yl]ethylamine trihydrochloride

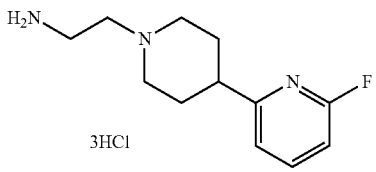 [SMILES: NCCN1CCC(c2cccc(F)n2)CC1]

According to the method of Reference examples 9-11, the title compound was prepared from 2-bromo-6-fluoropyridine.

$^1$H-NMR (400 MHz, DMSO-d$_6$) δ: 2.02-2.19 (4H, m), 2.91-3.06 (1H, m), 3.11-3.21 (2H, m), 3.31-3.44 (4H, m), 3.66 (2H, d, J=12.2 Hz), 7.05 (1H, dd, J=8.1, 2.7 Hz), 7.27 (1H, dd, J=7.4, 2.6 Hz), 7.97 (1H, dd, J=8.1, 8.1 Hz), 8.54 (3H, s), 11.04 (1H, s).

Reference Example 13

2-[4-(6-Methoxypyridin-2-yl)piperidin-1-yl]ethylamine trihydrochloride

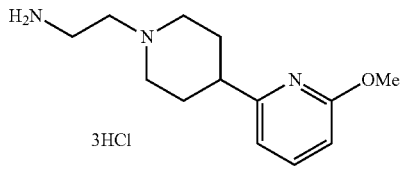 [SMILES: COc1cccc(C2CCN(CCN)CC2)n1]

According to the method of Reference examples 9-11, the title compound was prepared from 2-bromo-6-methoxypyridine.

$^1$H-NMR (300 MHz, D$_2$O) δ: 1.93-2.14 (2H, m), 2.19-2.33 (2H, m), 3.05-3.33 (3H, m), 3.39-3.55 (4H, m), 3.69-3.80 (2H, m), 4.02 (3H, s), 7.16 (2H, dd, J=15.3, 8.2 Hz), 8.13 (1H, d, J=8.7, 7.6 Hz).

Reference Example 14

2-{4-[6-(Difluoromethyl)pyridin-2-yl]piperidin-1-yl}ethylamine trihydrochloride

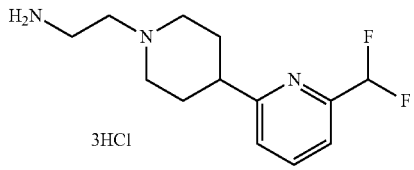 [SMILES: NCCN1CCC(c2cccc(C(F)F)n2)CC1]

According to the method of Reference examples 9-11, the title compound was prepared from 2-bromo-6-difluoromethylpyridine.

$^1$H-NMR (300 MHz, D$_2$O) δ: 1.78-1.92 (2H, m), 1.91-2.10 (2H, m), 2.63 (2H, t, J=12.1 Hz), 2.83-3.02 (3H, m), 3.09-3.33 (4H, m), 6.71 (1H, t, J=55.0 Hz), 7.41-7.50 (1H, m), 7.53 (1H, d, J=7.6 Hz), 7.86-7.96 (1H, m).

Reference Example 15

N-(2-{4-[(6E)-6-Hydrazinylidene-1,6-dihydropyridin-2-yl]piperidin-1-yl}ethyl)-tetrahydro-2H-pyran-4-carboxamide

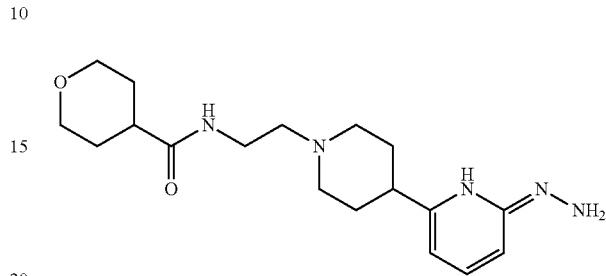

To a solution of the compound of Example 32 (300 mg) in 1,4-dioxane (2.0 mL) was added 50-60% aqueous hydrazine (2.9 mL), and the reaction mixture was stirred at 100° C. for 24 hours. The reaction mixture was concentrated, and dichloromethane (10 mL) was added thereto. The mixture was washed with brine (10 mL×2), and concentrated. The residue was purified by silica gel column chromatography (dichloromethane/methanol) to give the title compound (270 mg).

$^1$H-NMR (300 MHz, CDCl$_3$) δ: 1.63-1.90 (6H, m), 1.90-2.00 (2H, m), 2.14 (2H, td, J=11.7, 2.6 Hz), 2.39 (1H, tt, J=10.4, 5.3 Hz), 2.47-2.65 (3H, m), 2.91-3.06 (2H, m), 3.28-3.52 (4H, m), 4.05 (2H, td, J=11.5, 3.6 Hz), 5.74 (1H, s), 6.22 (1H, s), 6.52-6.62 (2H, m), 7.46 (1H, dd, J=8.2, 7.4 Hz).

Test 1: Evaluation of Agonistic Activity for Human 5-HT$_{1A}$ Receptor and Human D$_4$ Receptor Aequorin, Ga16 proteins, and each receptor were transiently expressed in CHO-K1 cell (Chinese hamster ovary), and seeded to 384-well plate. The plate was incubated in a CO$_2$ incubator at 37° C. for 24 hours. Each example compound dissolved in DMSO was added thereto, and the change of luminescence amount was measured with Hamamatsu FDSS/μCELL System (Hamamatsu Photonics). As for the agonistic activity, the maximum activity (E$_{max}$) of each compound was calculated on the assumption that the luminescence amount of the well without the compound is 0% and the luminescence amount of the well containing 10 μmol/L endogenous ligand is 100%. The results are shown in the table below.

| | 5-HT$_{1A}$ agonistic activity | | D$_4$ agonistic activity | |
|---|---|---|---|---|
| Example | EC$_{50}$ (nmol/L) | Emax (%) | EC$_{50}$ (nmol/L) | Emax (%) |
| 1 | <10 | 96 | 11.9 | 67 |
| 2 | 323 | 86 | 58.9 | 61 |
| 3 | 38 | 85 | 33.5 | 76 |
| 4 | <10 | 90 | 25.1 | 71 |
| 5 | 42 | 100 | 55.8 | 57 |
| 6 | 44 | 96 | <10 | 58 |
| 7 | <10 | 106 | <10 | 58 |
| 8 | <10 | 71 | 37.1 | 65 |
| 9 | <10 | 84 | <10 | 53 |
| 10 | 10 | 90 | 10 | 85 |
| 11 | 82 | 92 | 30.8 | 56 |

-continued

| Example | 5-HT$_{1A}$ agonistic activity | | D$_4$ agonistic activity | |
|---|---|---|---|---|
| | EC$_{50}$ (nmol/L) | Emax (%) | EC$_{50}$ (nmol/L) | Emax (%) |
| 12 | <10 | 43 | 35 | 52 |
| 13 | <10 | 48 | <10 | 55 |
| 14 | <10 | 41 | <10 | 53 |
| 15 | 100 | 33 | 41 | 55 |
| 16 | 43 | 36 | 31 | 51 |
| 17 | 94 | 30 | 44 | 51 |
| 18 | 68 | 43 | 37 | 61 |
| 19 | <10 | 65 | 9 | 84 |
| 20 | 57 | 40 | 15 | 60 |
| 21 | 84 | 30 | 65 | 62 |
| 22 | 595 | 25 | 57 | 57 |
| 23 | 632 | 28 | 62 | 59 |
| 24 | 67 | 50 | 32 | 62 |
| 25 | 67 | 46 | 30 | 49 |
| 26 | 395 | 43 | 3389 | 36 |
| 27 | 570 | 44 | 1648 | 51 |
| 28 | 47 | 69 | 37 | 44 |
| 29 | <10 | 50 | 24 | 74 |
| 30 | 27 | 36 | <10 | 59 |
| 31 | 35 | 40 | <10 | 52 |
| 32 | 67 | 51 | 7 | 67 |
| 33 | 22 | 83 | 13 | 62 |
| 34 | 22 | 42 | 15 | 55 |
| 35 | 525 | 27 | 64 | 52 |
| 36 | 279 | 38 | 31 | 58 |
| 37 | 343 | 40 | 52 | 57 |
| 38 | 86 | 50 | 42 | 35 |

Test 2: Evaluation of Binding Activity to Human 5-HT$_{1A}$ Receptor, Human D$_4$ Receptor, and Human D$_2$ Receptor The binding affinity of the present compounds to human 5-HT$_{1A}$ receptor, human D$_4$ receptor, and human D$_2$ receptor was measured in a manner mentioned below.

CHO cell membrane fraction in which human 5-HT$_{1A}$ receptor, human D$_4$ receptor, and human D$_2$ receptor were expressed was purchased from PerkinElmer Co., Ltd. In the evaluation test of binding, the test compound dissolved in DMSO, each receptor membrane preparation diluted with buffer solution, and [3H] 8-OH-DPAT (for 5-HT$_{1A}$ receptor), [3H] dopamine (for D$_4$ receptor), or [3H] spiperone (for D$_2$ receptor) (all were obtained from PerkinElmer Co., Ltd.) were mixed, and each mixture was incubated at room temperature for 30 or 60 minutes. The nonspecific binding to each receptor was evaluated by a competition binding experiment in the presence of 10 μmol/L 8-OH-DPAT, 10 μmol/L dopamine, or 10 μmol/L spiperone, respectively. The radioactivity of each receptor-binding sample was measured with a liquid scintillation counter (PerkinElmer Co., Ltd.), the 50% inhibitory concentration was calculated, and Ki value was evaluated based on the dissociation constant and the substrate concentration caluculated in the saturated bond test, which was used as binding affinity. The results are shown in the table below.

| Example | 5-HT$_{1A}$ (nmol/L) | D$_4$ (nmol/L) | D$_2$ (nmol/L) |
|---|---|---|---|
| 1 | 0.4 | 11 | 1144 |
| 2 | 11 | 109 | >10000 |
| 3 | 7.1 | 198 | >10000 |
| 4 | 0.4 | 26 | >10000 |
| 5 | 80 | 170 | >10000 |
| 6 | 37 | 101 | >10000 |
| 7 | 13 | 43 | >10000 |
| 8 | 1.4 | 111 | >10000 |
| 9 | 1.1 | 8.0 | 2443 |
| 10 | 1.4 | 19 | >10000 |
| 11 | 2.1 | 44 | >10000 |
| 12 | 0.2 | 4.5 | 357 |
| 13 | 1.1 | 24 | >10000 |
| 14 | 0.1 | 3.0 | 2438 |
| 15 | 13 | 505 | >10000 |
| 16 | 6 | 27 | 1688 |
| 17 | 26 | 91 | >10000 |
| 18 | 21 | 19 | 2209 |
| 19 | 0.8 | 8 | >10000 |
| 20 | 6.8 | 92 | >10000 |
| 21 | 15 | 201 | 2170 |
| 22 | 58 | 2241 | >10000 |
| 23 | 166 | 408 | >10000 |
| 24 | 27 | 3378 | >10000 |
| 25 | 20 | 423 | 3327 |
| 26 | 79 | 1902 | >10000 |
| 27 | 77 | 2474 | >10000 |
| 28 | 28 | 104 | 2472 |
| 29 | 0.4 | 22 | >10000 |
| 30 | 1.4 | 14 | >10000 |
| 31 | 0.3 | 2.9 | 1280 |
| 32 | 42 | 96 | >10000 |
| 33 | 21 | 119 | >10000 |
| 34 | 10 | 56 | >10000 |
| 35 | 278 | 2258 | >10000 |
| 36 | 132 | 120 | >10000 |
| 37 | 108 | 73 | >10000 |
| 38 | 37 | 10 | >10000 |

Test 3-1: Metabolic Stability Test of Human Liver Microsome

The stability of the present compounds for human liver microsome metabolism was evaluated as mentioned below. The used human liver microsome was obtained from Xenotech. Human liver microsome, NADPH, and each test compound were mixed in 25 mmol/L phosphate buffer solution (pH 7.4) to adjust each concentration as shown below, and the mixture was incubated at 37° C. for 30 minutes.

human liver microsome: 0.1 mg/mL
NAPDH: 3.2 mmol/L
test compound: 0.1 μmol/L

The residual ratio of the test compound in each sample after the incubation for 30 minutes was measured with a LC-MS, and the metabolic stability of human liver microsome was calculated about each test compound with the following formula.

Metabolic stability of human liver microsome(mL/min/mg protein)=−LN(residual ratio)/"reaction time"/"concentration of human liver microsome"

The results are shown in the table below.

| Example | Metabolic stability of human liver microsome (mL/min/mg protein) |
|---|---|
| 1 | 0.073 |
| 2 | 0.069 |
| 3 | <0.01 |
| 4 | <0.01 |
| 5 | <0.01 |
| 6 | <0.01 |
| 7 | 0.017 |
| 8 | 0.017 |
| 9 | 0.025 |
| 10 | 0.015 |
| 11 | <0.01 |
| 12 | 0.115 |
| 13 | <0.05 |

| Example | Metabolic stability of human liver microsome (mL/min/mg protein) |
| --- | --- |
| 14 | 0.084 |
| 15 | <0.05 |
| 16 | <0.05 |
| 18 | <0.05 |
| 20 | <0.05 |
| 21 | <0.05 |
| 25 | <0.05 |
| 28 | <0.05 |
| 29 | <0.05 |
| 30 | 0.114 |
| 31 | <0.05 |
| 33 | <0.05 |
| 34 | <0.05 |
| 38 | <0.05 |

Test 3-2: Metabolic Stability Test of Human Liver Microsome

In order to evaluate the metabolic stability of human liver microsomes more precisely, the stability of the present compounds for human liver microsome metabolism was evaluated with a suitable concentration of human liver microsome, as mentioned below. The used human liver microsome was obtained from Xenontech. Human liver microsome, NADPH, and each test compound were mixed in 25 mmol/L phosphate buffer solution (pH 7.4) to adjust each concentration as shown below, and the mixture was incubated at 37° C. for 30 minutes.

human liver microsome: 0.5 or 1.0 mg/mL
NAPDH: 3.2 mmol/L
test compound: 0.1 μmol/L The residual ratio of the test compound in each sample after the incubation for 30 minutes was measured with a LC-MS, and the metabolic stability of human liver microsome was calculated about each test compound with the following formula.

Metabolic stability of human liver microsome(mL/min/mg protein)=−LN(residual ratio)/"reaction time"/"concentration of human liver microsome"

The results are shown in the table below.

| Example | Metabolic stability of human liver microsome (mL/min/mg protein) |
| --- | --- |
| 1 | 0.031 |
| 8 | 0.023 |
| 9 | 0.016 |
| 11 | 0.0075 |

Test 4-1: Predictive Test of Human Half-Life

The disappearance half-life of the present compounds in human was predicted in a manner mentioned below. 0.01 mol/L of the present compound in aqueous hydrochloric acid solution was parenterally administered to cynomolgus monkey. 5 minutes, 15 minutes, 30 minutes, 1 hour, 2 hours, 4 hours, 6 hours, and 24 hours after the administration, the blood was collected. The plasma was obtained from the collected blood, the drug concentration in the plasma was measured with a LC-MS, and the monkey distribution volume was calculated from the transition of the concentrations. The unbound fraction rate of the present compound in serum of human and monkey was measured by equilibrium dialysis method.

Using the monkey distribution volume, the unbound fraction rate in serum of human and monkey, and the result of the metabolic stability of human liver microsome which was obtained in Test 3-1, the half-life in human was calculated according to the formula below.

"Human distribution volume"="monkey distribution volume"×"unbound fraction rate in serum of human"/"unbound fraction rate in serum of monkey"

"Human hepatic clearance"=("human hepatic blood flow"×"unbound fraction rate in serum of human"×56.7×"metabolic stability of human liver microsome")/("human hepatic blood flow"+"unbound fraction rate in serum of human"×56.7×"metabolic stability of human liver microsome")

"Half-life in human"=0.693×"human distribution volume"/"human hepatic clearance"

The results are shown in the table below.

| Example | Half-life in human (h) |
| --- | --- |
| 1 | 11 |
| 8 | 9.2 |
| 11 | 13 |

Test 4-2: Predictive Test of Human Half-Life

In order to estimate the disappearance half-life of the present compounds in human more precisely, the half life was predicted by using the result of the metabolic stability of human liver microsome which was obtained in Test 3-2, in a manner mentioned below.

0.01 mol/L of the present compound in aqueous hydrochloric acid solution was parenterally administered to cynomolgus monkey. 5 minutes, 15 minutes, 30 minutes, 1 hour, 2 hours, 4 hours, 6 hours, and 24 hours after the administration, the blood was collected. The plasma was obtained from the collected blood, the drug concentration in the plasma was measured with a LC-MS, and the monkey distribution volume was calculated from the transition of the concentrations. The unbound fraction rate of the present compound in serum of human and monkey was measured by equilibrium dialysis method.

Using the monkey distribution volume, the unbound fraction rate in serum of human and monkey, and the result of the metabolic stability of human liver microsome which was obtained in Test 3-2, the half-life in human was calculated according to the formula below.

"Human distribution volume"="monkey distribution volume"×"unbound fraction rate in serum of human"/"unbound fraction rate in serum of monkey"

"Human hepatic clearance"=("human hepatic blood flow"×"unbound fraction rate in serum of human"×56.7×"metabolic stability of human liver microsome")/("human hepatic blood flow"+"unbound fraction rate in serum of human"×56.7×"metabolic stability of human liver microsome")

"Half-life in human"=0.693×"human distribution volume"/"human hepatic clearance"

The results are shown in the table below.

| Example | Half-life in human (h) |
|---|---|
| 1 | 24 |
| 8 | 59 |
| 11 | 17 |
| 9 | 10 |

Test 5-1: Evaluation of Activity for Inhibiting hERG Channel

The activity of the present compound for inhibiting hERG channel was measured by whole-cell patch clamp method with auto patch clamp system, using CHO cell wherein hERG channel involved in human rapidly activating delayed rectifier potassium current ($I_{Kr}$) was forcibly expressed.

(Preparation of Cell Suspension)

hERG-CHO cell purchased from ChanTest was incubated at 37° C. in a $CO_2$ incubator, and the cell was exfoliated from the flask with trypsin to prepare a cell suspension, shortly before the hERG current measurement.

(Preparation of Solution)

The extracellular fluid and intracellular fluid which were used in the measurement were prepared as follows.

Extracellular fluid: 2 mmol/L $CaCl_2$, 1 mmol/L $MgCl_2$, 10 mmol/L HEPES, 4 mmol/L KCl, 145 mmol/L NaCl, 10 mmol/L glucose Intracellular fluid: 5.4 mmol/L $CaCl_2$, 1.8 mmol/L $MgCl_2$, 10 mmol/L HEPES, 31 mmol/L KOH, 10 mmol/L EGTA, 120 mmol/L KCl, 4 mmol/L $Na_2$-ATP Test compound solution: The test compound was dissolved in DMSO by adjusting the concentration to 2 mmol/L or 20 mmol/L to prepare each test compound solution. Further, the test compound solution was diluted with the extracellular fluid by 200-fold, which was serially diluted with the extracellular fluid to prepare each concentration of the test compound solution which is used to calculate $IC_{50}$ value of hERG inhibition.

(Measurement of Current Value and Data Analysis)

The cell suspension, the extracellular fluid, the intracellular fluid, and the measurement plate were set in an auto patch clamp system, and the hERG current was measured by whole-cell patch clamp method. The voltage-protocol was as follows: the holding potential was adjusted to −80 mV, the depolarizing pulse was added at −50 mV to +20 mV for 5 seconds, the repolarizing pulse was added at −50 mV for 5 seconds, then the potential was returned to the holding potential. Each pulse interval was 15 seconds. The data analysis was carried out with Qpatch Assay Software (Biolin Scientific). The test was carried out applying increscently 4 concentrations of each test compound, and the average of the peak tail currents that were obtained by the last 3 stimulations in each applied concentration was determined to be the evaluated data. By using the current inhibition rate for the pre-applied current at each concentration of each test compound, $IC_{50}$ value was calculated by Hill equation with the software.

The results are shown in the table below.

| Example | hERG inhibition $IC_{50}$ (μmol/L) |
|---|---|
| 1 | 2.5 |
| 2 | >10 |
| 3 | 32.1 |
| 4 | 4.0 |
| 5 | 48.2 |
| 6 | 12.8 |
| 7 | 5.6 |
| 8 | 44.3 |
| 9 | 5.9 |
| 10 | >10 |
| 11 | 12.7 |

Test 5-2: Evaluation of Activity for Inhibiting hERG Channel

The activity of the present compound for inhibiting hERG channel was measured by whole-cell patch clamp method with auto patch clamp system, using CHO cell wherein hERG channel involved in human rapidly activating delayed rectifier potassium current ($I_{Kr}$) was forcibly expressed.

(Preparation of Cell Suspension)

hERG-CHO cell purchased from ChanTest was incubated at 37° C. in a $CO_2$ incubator, and the cell was exfoliated from the flask with trypsin to prepare a cell suspension, shortly before the hERG current measurement.

(Preparation of Solution)

The extracellular fluid and intracellular fluid which were used in the measurement were prepared as follows.

Extracellular fluid: 2 mmol/L $CaCl_2$, 1 mmol/L $MgCl_2$, 10 mmol/L HEPES, 4 mmol/L KCl, 145 mmol/L NaCl, 10 mmol/L glucose Intracellular fluid: 10 mmol/L HEPES, 10 mmol/L EGTA, 20 mmol/L KCl, 130 mmol/L KF Test compound solution: The compound was dissolved in DMSO by adjusting the concentration to 2 mmol/L or 20 mmol/L to prepare each test compound solution. Further, the test compound solution was diluted with the extracellular fluid by 200-fold, which was serially diluted with the extracellular fluid to prepare each concentration of the test compound solution which is used to calculate $IC_{50}$ value of hERG inhibition.

(Measurement of Current Value and Data Analysis)

The cell suspension, the extracellular fluid, the intracellular fluid, and the measurement plate were set in an auto patch clamp system, and the hERG current was measured by whole-cell patch clamp method. The voltage-protocol was as follows: the holding potential was adjusted to −80 mV, the depolarizing pulse was added at −50 mV to +20 mV for 5 seconds, the repolarizing pulse was added at −50 mV for 5 seconds, then the potential was returned to the holding potential. Each pulse interval was 15 seconds. The data analysis was carried out with Qube Assay Software (Sophion Scientific). The test was carried out applying increscently 4 concentrations of each test compound, and the average of the peak tail currents that were obtained by the last 3 stimulations in each applied concentration was made to be the evaluated data. By using the current inhibition rate for the pre-applied current at each concentration of each test compound, $IC_{50}$ value was calculated by Hill equation with the software.

The results are shown in the table below.

| Example | hERG inhibition $IC_{50}$ (μmol/L) |
|---|---|
| 12 | 3.5 |
| 13 | >10 |
| 14 | 8.1 |
| 15 | >10 |
| 16 | >10 |
| 18 | >10 |

-continued

| Example | hERG inhibition IC$_{50}$ (µmol/L) |
|---|---|
| 20 | >10 |
| 21 | >10 |
| 25 | >10 |
| 28 | >10 |
| 29 | >10 |
| 30 | >10 |
| 31 | >10 |
| 33 | >10 |
| 34 | 5.5 |
| 38 | >10 |

Test 6: Contextual Fear Conditioning Test

The antianxiety of the present compounds was evaluated in a manner mentioned below.

The evaluation of an 8-week-old SD male rat with a fear conditioning test system (O'HARA & CO., LTD.) was carried out in 2-day test schedule. On the 1st day of the test, by giving 0.5 mA of electric shock to the rat as unconditioned stimulus 5 times for 6 minutes, the rat was made to learn the relationship the context (the illuminance in the cage: 200 1x) which was given as conditioned stimulus, and phobic stimulus. On the 2nd day, the present compound was subcutaneously administered with saline solution to the rat, or orally administered with methylcellulose suspension to the rat. 0.5 or 1 hour after the administration, the rat was made to softly enter the cage under the condition in which the unconditioned stimulus was not given in the context. The time of cataleptic freezing reaction that the rat took for 5-minute freely-moving period and its ratio were measured. The ratios of cataleptic freezing reaction between the solvent-administration group and the present compound-administration group were compared to be statistically processed. The compound-administration groups of Example 1 (15 mg/kg administration), Example 8 (10 mg/kg administration), and Example 11 (30 mg/kg administration) showed 82.5%, 41.0%, and 65.5% decreases of the cataleptic freezing reaction for the solvent-administration group, respectively (see, FIG. 1).

Test 7: Marble-Burying Behavior Test

The effect of the present compound for obsessive-compulsive disorder-like behavior was evaluated in a manner mentioned below.

Figure 2:
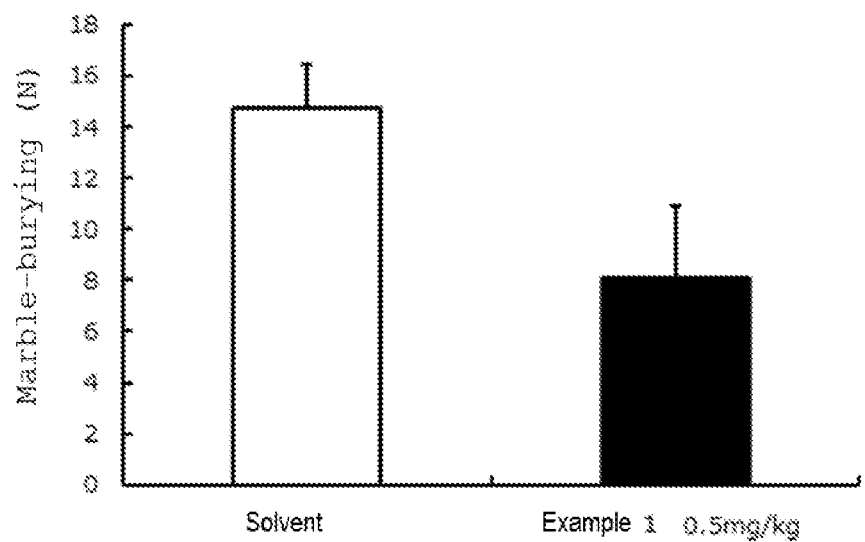
FIG. 2 shows the results of the compounds of Examples 1 and 11 in the marble-burying behavior test (Test 7).
Figure 2:
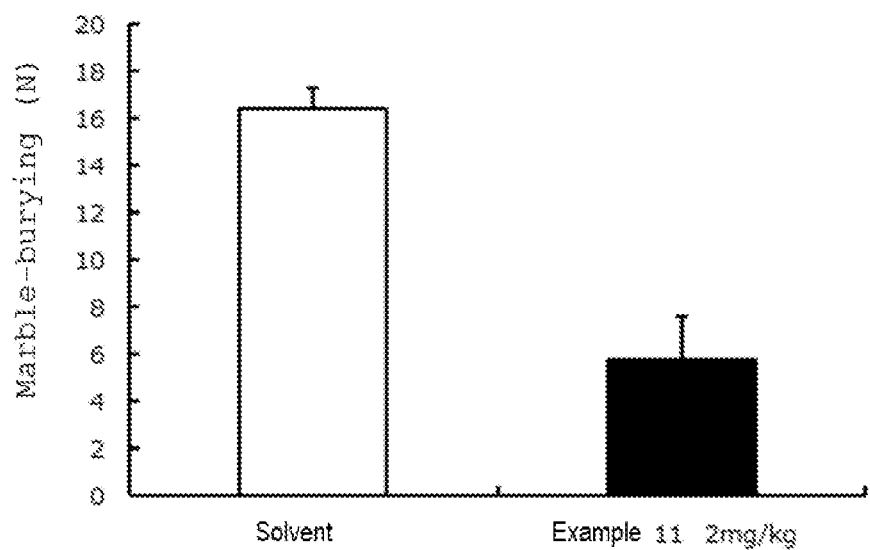

450-500 g of paper floorcloth was beded in a plastic cage (floor area: 778 cm$^2$), and 20 glass marbles were set on the paper floorcloth at regular intervals. To a 5-week-old ICR male mouse, the present compound was intraperitoneally administered with saline solution. 15 minutes after the administration, the mouse was made to softly enter the corner of the cage and move freely in the cage for 15 minutes. Then the mouse was taken out from the cage. The number of the marbles that were buried in the floorcloth was counted. The numbers in the solvent-administration group and the present compound-administration group were compared to be statistically processed. The compound-administration groups of Example 1 (0.5 mg/kg administration) and Example 11 (2 mg/kg administration) showed 44.8% and 64.8% decreases of the buried marbles in the floorcloth for the solvent-administration group, respectively (see, FIG. 2).

Figure 3:
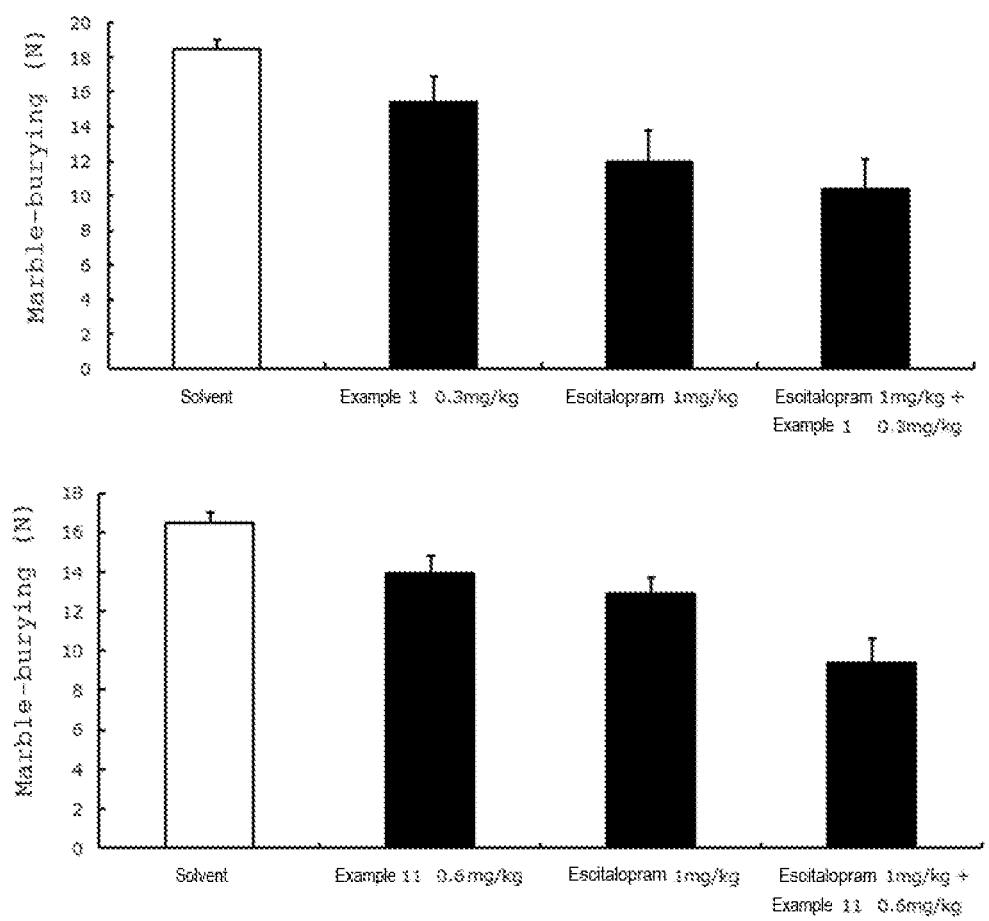
FIG. 3 shows the results of the combination of the compound of Example 1 and escitalopram, and the combination of the compound of Example 11 and escitalopram in marble-burying behavior test (Test 7).

In addition, compared with the result of single administration of escitalopram which is a typical selective serotonin reuptake inhibitor, the combination of escitalopram and the present compound of Example 1 (0.3 mg/kg administration) or Example 11 (1 mg/kg administration) showed significant enhancement effect of decreasing the number of the buried marbles (43.8%, 42.9%) (see, FIG. 3)

Test 8: Forced Swimming Test

The antidepressive effect of the present compound was evaluated in a manner mentioned below.

Figure 4:
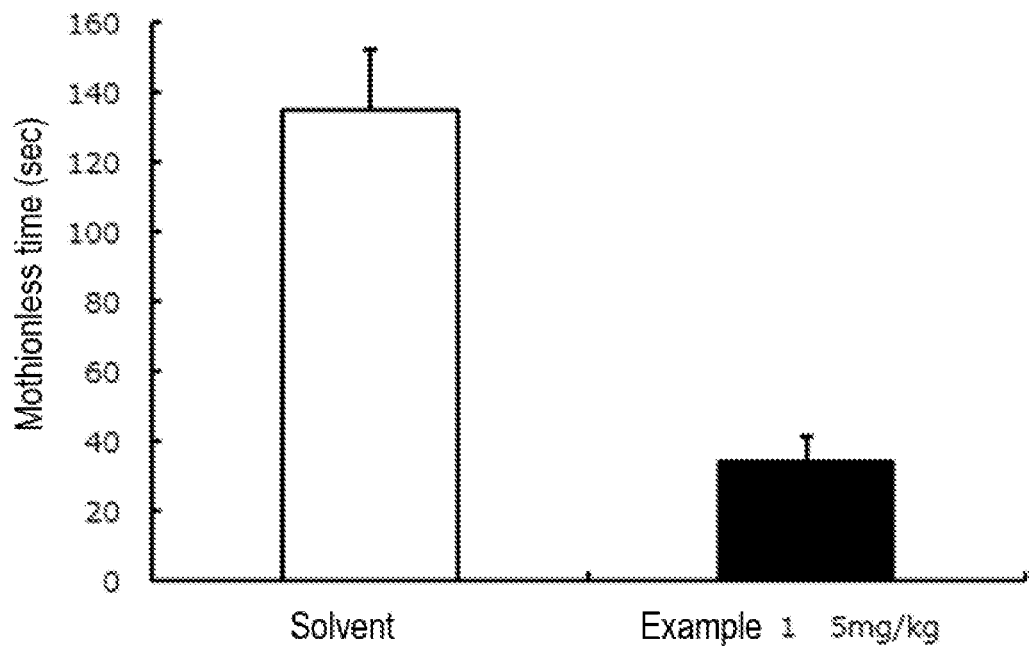
FIG. 4 shows the results of the compounds of Examples 1 and 11 in the forced swimming test (Test 8).
Figure 4:
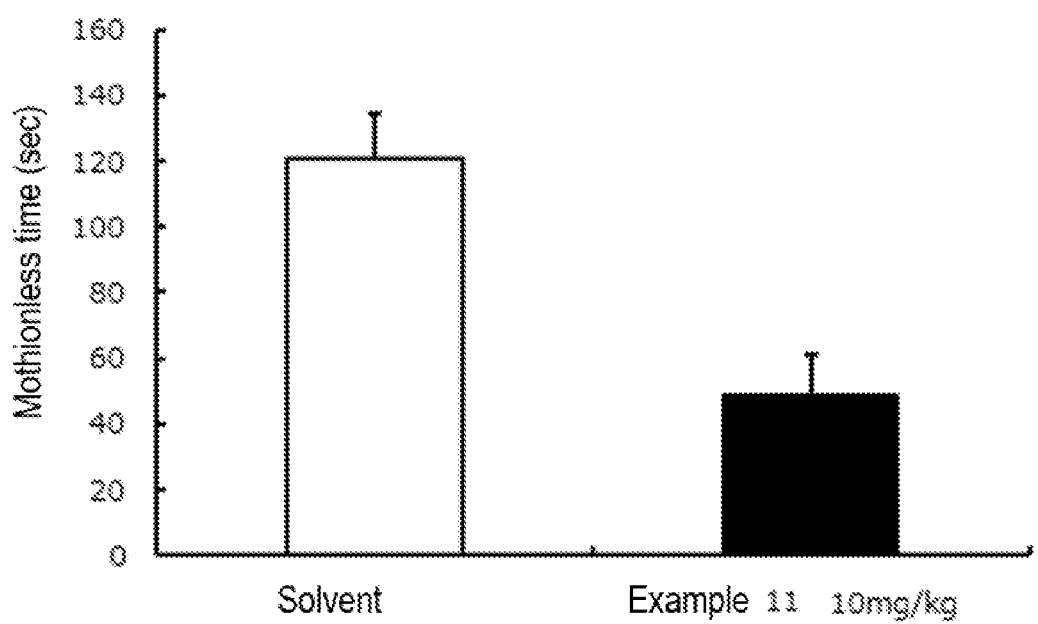

The test was carried out with 8-week-old Wistar male rat in 4-day test schedule. On the 1st day of the test, the rat was put into a transparent plastic bath filled with 5.8 L of tap water at 25° C., and made to swim for 15 minutes as swimming training. After the swimming training, the rat was rapidly wiped to remove the attached waterdrop, and returned to the home cage. 15 minutes after the training, the present compound or a positive control compound was orally administered with methylcellulose suspension to the rat. On the next day of the training and the day after next, the present compound or the positive control compound was orally administered with methylcellulose suspension to the rat once a day. On the 4th day, the swimming test was carried out. On the day of the swimming test, the present compound or the positive control compound was orally administered with methylcellulose suspension to the rat one hour before the start of the test. The swimming test was carried out with the rat in the above-mentioned water bath for 5 minutes. The swimming movement of the individual was recorded with a video from the side of the water bath, and the immobility time was measured with a stop-watch. The immobility used herein means a state that the animal is floating in the water bath without moving the forelimbs and torso, and it was judged that insensible movement for keeping its floating pose was immobility. The accumulated time of immobility was defined as immobility time for the individual. The immobility times of the solvent-administration group and the present compound-administration group were compared to be statistically processed. The compound-administration groups of Example 1 (5 mg/kg administration) and Example 11 (10 mg/kg administration) showed 74.7% and 59.2% decreases of the immobility time for the solvent-administration group, respectively (see, FIG. 4).

Test 9: Microdialysis Test

The effect of the present compound for the release amount of intracerebral monoamine was evaluated in a manner mentioned below.

Figures 1, 5:
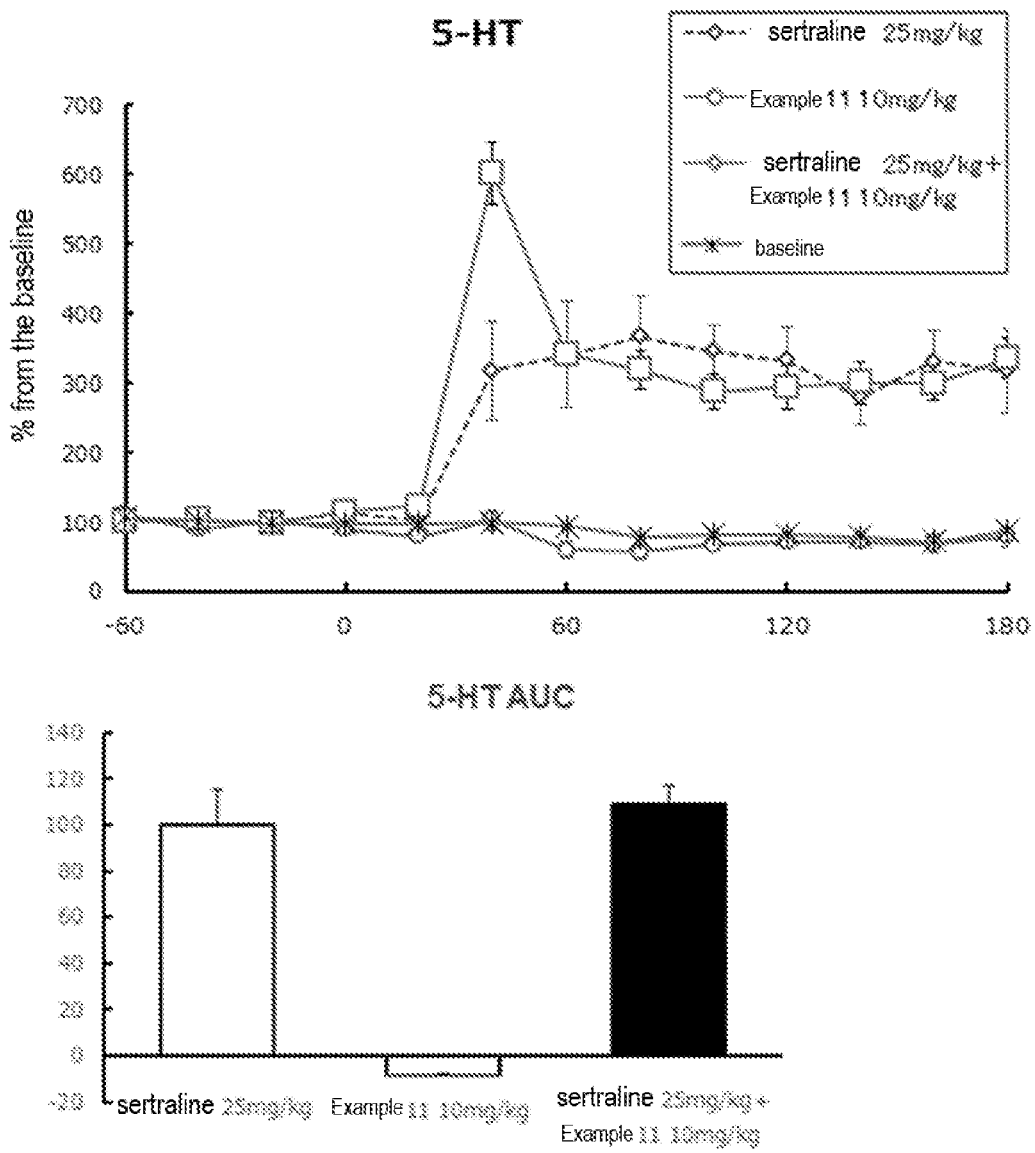
FIG. 5 shows the results of the compound of Example 11, and the combination of the compound of Example 11 and sertraline in the microdialysis test (Test 9).
Figures 2, 5:
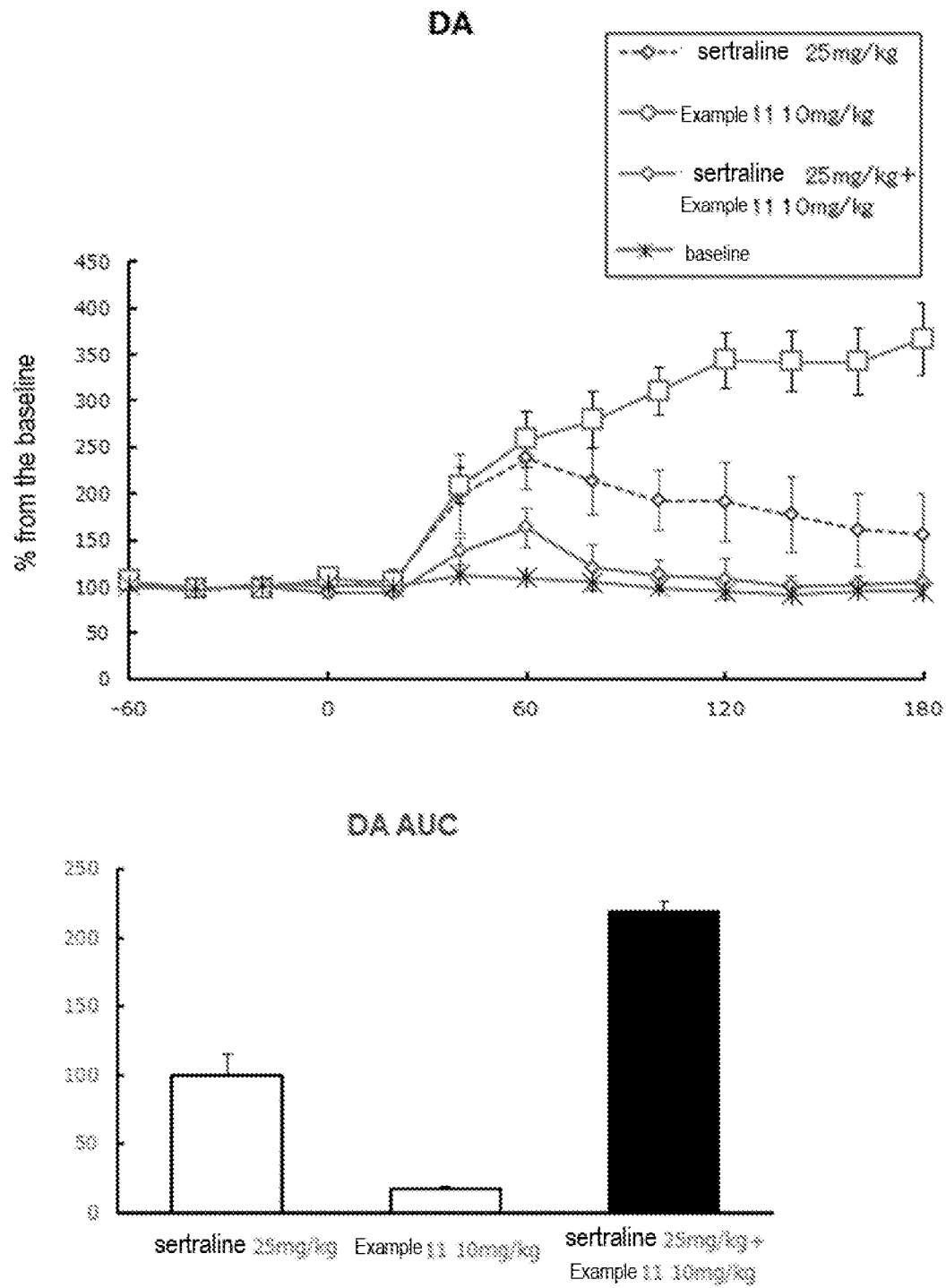
Figures 3, 5:
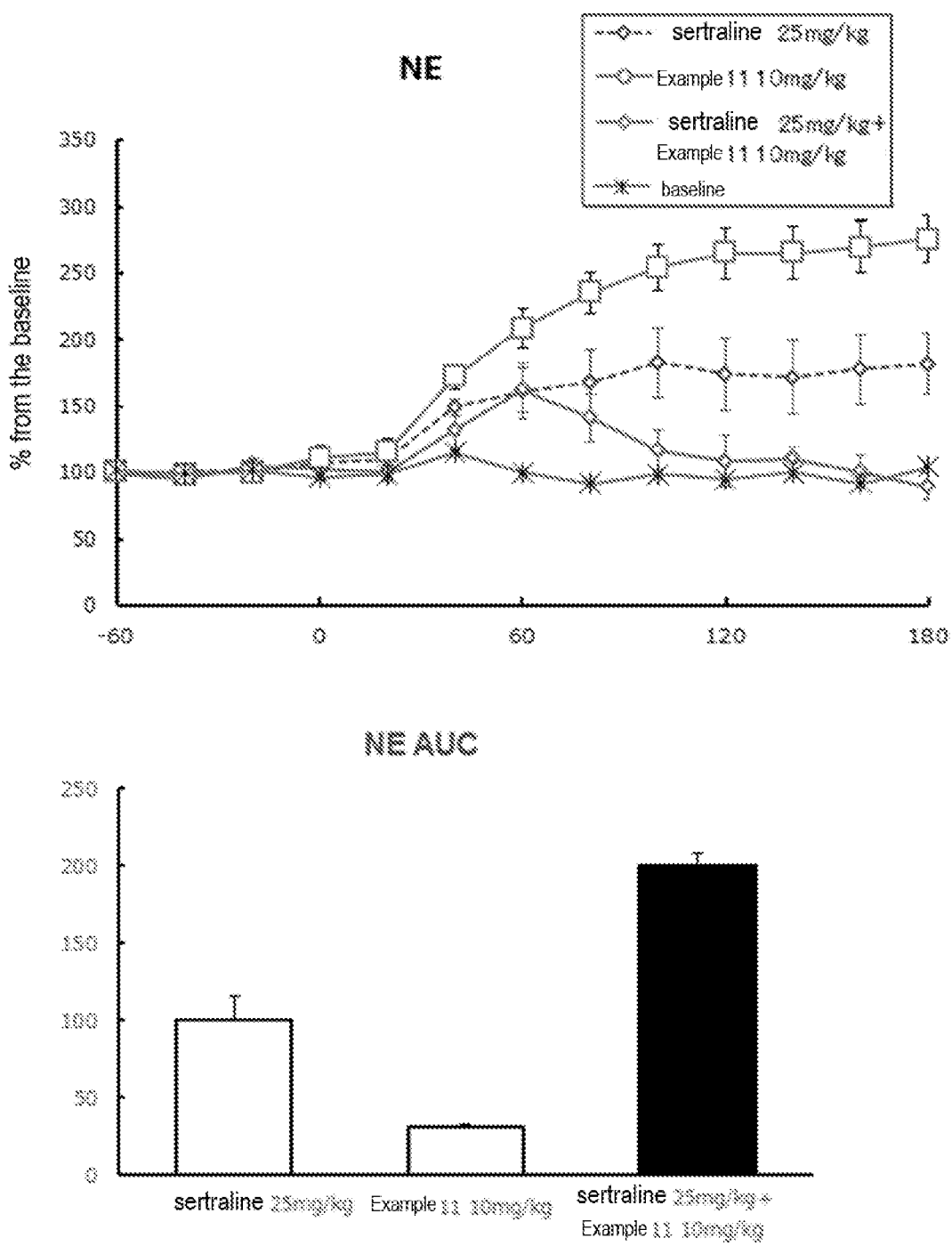

8-Week-old Wistar male rat was fixed on a brain stereotaxic apparatus under anesthesia. The scalp was incised, the subcutaneous tissue was removed, the position of the bregma was measured, and the installation position of a guide cannula was calculated (the position of the orbitofrontal cortex which defined according to the brain stereotaxic coordinates of Paxinos & Watson (2.0 mm right, 4.2 mm anterior from bregma)). The skull was drilled with a dental drill at the installation position of the guide cannula, and an anchor screw was set about 1 cm posterior to the hole. The guide cannula was set and fixed with a dental cement, and then the scalp was sutured. The animal was released from the brain stereotaxic apparatus, and was moved back to the breeding cage. In the event of the test, the rat was put in an acrylic observable cage, and a dialysis probe was inserted along the guide cannula to connect to a free-moving tube. With an infusion pump, Ringer solution was perfused at 2 µL/min, and the dialysis solution was recovered at 20-minute intervals. After 3 samples from the 1st recovery were recovered, the present compound was orally administered with methylcellulose suspension to the rat. Until 180 minutes after the administration, the dialysis solutions were recovered (9 samples). The recovered dialysis solutions were analyzed with a HPLC-ECD system to determine the contents of norepinephrine (NE), dopamine (DA), and serotonin (5-HT). The compound group of Example 11 (10 mg/kg administration) showed a decrese of the serotonin content in the dialysis solution (20.6%) and increases of the norepinephrine and dopamine contents in the dialysis solution (18.3%, 12.4%), compared with the solvent-administration group. In addition, the combination administration of sertraline and Example 11 (10 mg/kg administration) showed significant increases of norepinephrine and dopamine in the dialysis solution (100%, 119%), compared with the result of the single administration of sertraline (see, FIG. 5).

It is known that the single administration of a serotonin $5\text{-HT}_{1A}$ agonist can decrease the serotonin content. On the other hand, when a serotonin $5\text{-HT}_{1A}$ agonist is repetitively administered, the sensitivity of the autoreceptor can lower to deactivate the inhibition of the serotonin release. Thus, it is thought that the antidepressive effect can be exerted (Neuroscience. 1999, 93(4): 1251-1262, Neurochem Int. 2002, 40(4): 355-360). Example 11 did not decrease the serotonin content in the combination administration with sertraline or in single administration. Considering the results, the present compound is expected to exert the potentiation of antidepressive effect through the combination administration with sertraline, which is very different from other serotonin $5\text{-HT}_{1A}$ agonists.

INDUSTRIAL APPLICABILITY

The present compound has dual agonism for serotonin $5\text{-HT}_{1A}$ receptor and dopamine $D_4$ receptor, and thereby the present compound is useful as a medicament for treating symptoms in anxiety-related disorder.

The invention claimed is:
1. A compound of formula (1):

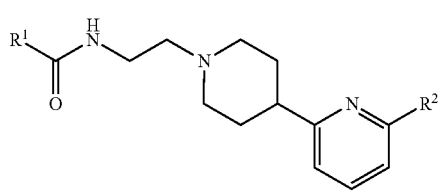

(1)

or a pharmaceutically acceptable salt thereof, wherein
$R^1$ is optionally-substituted $C_{1-6}$ alkyl, optionally-substituted $C_{3-10}$ cycloalkyl, or optionally-substituted 5- to 10-membered saturated or partially-unsaturated heterocyclyl group; and
$R^2$ is halogen atom, cyano, $C_{1-6}$ alkyl which may be optionally substituted with 1 to 3 the same or different halogen atoms, $C_{1-6}$ alkoxy which may be optionally substituted with 1 to 3 the same or different halogen atoms, or amino which may be optionally substituted with 1 or 2 the same or different $C_{1-6}$ alkyl groups.

2. The compound of claim 1 or a pharmaceutically acceptable salt thereof, wherein
$R^1$ is
(1) $C_{1-6}$ alkyl which may be optionally substituted with 1 to 3 the same or different substituents selected from the group consisting of halogen atom, hydroxy, $C_{3-7}$ cycloalkyl, and $C_{1-6}$ alkoxy,
(2) $C_{3-10}$ cycloalkyl which may be optionally substituted with 1 to 4 the same or different substituents selected from the group consisting of halogen atom, hydroxy, cyano, $C_{1-6}$ alkyl which may be optionally substituted with 1 to 3 the same or different halogen atom or $C_{1-6}$ alkoxy, $C_{1-6}$ alkoxy which may be optionally substituted with 1 to 3 the same or different halogen atom or $C_{1-6}$ alkoxy, and amino which may be optionally substituted with 1 or 2 the same or different $C_{1-6}$ alkyl, or
(3) 5- to 10-membered saturated or partially-unsaturated heterocyclyl group which may be optionally substituted with 1 to 4 the same or different substituents selected from the group consisting of halogen atom, hydroxy, cyano, $C_{1-6}$ alkyl which may be optionally substituted with 1 to 3 the same or different halogen atom or $C_{1-6}$ alkoxy, $C_{1-6}$ alkoxy which may be optionally substituted with 1 to 3 the same or different halogen atom or $C_{1-6}$ alkoxy, and amino which may be optionally substituted with 1 or 2 the same or different $C_{1-6}$ alkyl.

3. The compound of claim 1, or a pharmaceutically acceptable salt thereof, wherein
$R^1$ is
(1) $C_{3-7}$ cycloalkyl which may be optionally substituted with 1 to 4 the same or different substituents selected from the group consisting of halogen atom, and $C_{1-6}$ alkyl which may be optionally substituted with 1 to 3 the same or different halogen atom or $C_{1-6}$ alkoxy, or
(2) 5- or 6-membered saturated or partially-unsaturated heterocyclyl group which may be optionally substituted with 1 to 4 the same or different substituents selected from the group consisting of halogen atom, and $C_{1-6}$ alkyl which may be optionally substituted with 1 to 3 the same or different halogen atom or $C_{1-6}$ alkoxy.

4. The compound of claim 1, or a pharmaceutically acceptable salt thereof, wherein $R^1$ is $C_{3-7}$ cycloalkyl which may be optionally substituted with 1 to 4 fluorine atoms, or 5- or 6-membered saturated or partially-unsaturated heterocyclyl group which may be optionally substituted with 1 to 4 fluorine atoms.

5. The compound of claim 1, or a pharmaceutically acceptable salt thereof, wherein $R^1$ is cyclohexyl which may be optionally substituted with 1 to 4 fluorine atoms, tetrahydropyranyl, tetrahydrofuryl, dihydropyranyl, or dihydrofuryl.

6. The compound of claim 1, or a pharmaceutically acceptable salt thereof, wherein $R^1$ is difluorocyclohexyl, or tetrahydropyranyl.

7. The compound of claim 1, or a pharmaceutically acceptable salt thereof, wherein $R^2$ is halogen atom, or $C_{1-6}$ alkyl which may be optionally substituted with 1 to 3 the same or different halogen atoms.

8. The compound of claim 1, or a pharmaceutically acceptable salt thereof, wherein $R^2$ is $C_{1-4}$ alkyl which may be optionally substituted with 1 to 3 fluorine atoms.

9. The compound of claim 1, which is selected from the group consisting of:
4,4-difluoro-N-(2-{4-[6-(trifluoromethyl)pyridin-2-yl]piperidin-1-yl}ethyl)cyclohexane-carboxamide,
N-{2-[4-(6-methylpyridin-2-yl)piperidin-1-yl]ethyl}-tetrahydro-2H-pyran-4-carboxamide,
2,2-dimethyl-N-(2-{4-[6-(trifluoromethyl)pyridin-2-yl]piperidin-1-yl}ethyl)propanamide, and
N-(2-(4-[6-(trifluoromethyl)pyridin-2-yl]piperidin-1-yl)ethyl)-tetrahydro-2H-pyran-4-carboxamide,
or a pharmaceutically acceptable salt thereof.

10. The compound of claim 1, which is 2,2-dimethyl-N-(2-{4-[6-(trifluoromethyl)pyridin-2-yl]piperidin-1-yl}ethyl)propanamide, or a pharmaceutically acceptable salt thereof.

11. A medicament comprising the compound of claim 1 or a pharmaceutically acceptable salt thereof as an active ingredient, and a pharmaceutically acceptable excipient, additive and/or carrier.

12. A method for treating a disease or disorder selected from the group consisting of generalized anxiety disorder, major depression, obsessive-compulsive disorder, Parkinson's disease, and Rett syndrome, the method comprising administering a therapeutically effective amount of the compound of claim 1 or a pharmaceutically acceptable salt thereof to a patient in need thereof.

13. A medicament comprising the compound of claim 1 or a pharmaceutically acceptable salt thereof, and at least one other medicament selected from drugs classified as an antianxiety drug or an antidepressant drug.

14. The medicament of claim 13, wherein the antianxiety drug is a selective serotonin reuptake inhibitor.

15. The medicament of claim 14, wherein the selective serotonin reuptake inhibitor is at least one drug selected from the group consisting of sertraline, escitalopram, fluvoxamine, fuoxetine, paroxetine, clomipramine, and pharmaceutically acceptable salts thereof.

16. The medicament of claim 13, wherein the antidepressant drug is a serotonin reuptake inhibitor.

17. The medicament of claim 16, wherein the serotonin reuptake inhibitor is at least one drug selected from the group consisting of milnacipran, duloxetine, venlafaxine, amoxapine, clomipramine, nortriptyline, imipramine, vortioxetine, and pharmaceutically acceptable salts thereof.

18. The method of claim 12, wherein the compound is 4,4-difluoro-N-(2-{4-[6-(trifluoromethyl)pyridin-2-yl]piperidin-1-yl-}ethyl)cyclohexane-carboxamide, or a pharmaceutically acceptable salt thereof.

19. The method of claim 12, wherein the compound is N-{2-[4-(6-methylpyridin-2-yl)piperidin-1-yl]ethyl}-tetrahydro-2H-pyran-4-carboxamide, or a pharmaceutically acceptable salt thereof.

20. The method of claim 12, wherein the compound is N-(2-{4-[6 -(trifluoromethyl)pyridin-2-yl]piperidin-1-yl}ethyl)-tetrahydro-2H-pyran-4-carboxamide, or a pharmaceutically acceptable salt thereof.

21. The method of claim 12, wherein the disease or disorder is generalized anxiety disorder, major depression, or obsessive-compulsive disorder.

22. The method of claim 18, wherein the disease or disorder is generalized anxiety disorder, major depression, or obsessive-compulsive disorder.

23. The method of claim 19, wherein the disease or disorder is generalized anxiety disorder, major depression, or obsessive-compulsive disorder.

24. The method of claim 20, wherein the disease or disorder is generalized anxiety disorder, major depression, or obsessive-compulsive disorder.

* * * * *